US012747292B2

(12) United States Patent
Endell et al.

(10) Patent No.: US 12,747,292 B2
(45) Date of Patent: Sep. 29, 2026

(54) ANTI-TUMOR COMBINATION THERAPY COMPRISING ANTI-CD19 ANTIBODY AND GAMMA DELTA T-CELLS

(71) Applicant: Incyte Corporation, Wilmington, DE (US)

(72) Inventors: Jan Endell, Munich (DE); Rainer Boxhammer, Kolbermoor (DE); Dominik Pretscher, Würzburg (DE)

(73) Assignee: Incyte Corporation, Wilmington, DE (US)

( * ) Notice: Subject to any disclaimer, the term of this patent is extended or adjusted under 35 U.S.C. 154(b) by 0 days.

(21) Appl. No.: 17/084,783

(22) Filed: Oct. 30, 2020

(65) Prior Publication Data

US 2021/0130461 A1 May 6, 2021

(30) Foreign Application Priority Data

Oct. 31, 2019 (EP) .................................... 19206479

(51) Int. Cl.
*C07K 16/28* (2006.01)
*A61K 40/11* (2025.01)
*A61K 40/32* (2025.01)
*A61K 40/42* (2025.01)

(52) U.S. Cl.
CPC .......... *C07K 16/2803* (2013.01); *A61K 40/11* (2025.01); *A61K 40/32* (2025.01); *A61K 40/42* (2025.01); *A61K 2239/48* (2023.05); *C07K 2317/565* (2013.01)

(58) Field of Classification Search
CPC .......... C07K 16/2803; C07K 2317/565; C07K 2317/732; A61K 35/17; A61K 39/395; A61K 2039/505; A61K 2300/00; A61K 39/4644; A61P 35/02
See application file for complete search history.

(56) References Cited

U.S. PATENT DOCUMENTS

| | | | |
|---|---|---|---|
| 5,641,870 | A | 6/1997 | Rinderknecht et al. |
| 6,703,199 | B1 | 3/2004 | Koide |
| 7,109,304 | B2 | 9/2006 | Hansen et al. |
| 7,635,472 | B2 | 12/2009 | Kufer et al. |
| 8,097,703 | B2 | 1/2012 | Rao-Naik et al. |
| 8,524,867 | B2 | 9/2013 | Bernett et al. |
| 9,499,788 | B2 | 11/2016 | de Carvalho e Silva Santos et al. |
| 9,803,020 | B2 | 10/2017 | Bernett et al. |
| 2007/0154473 | A1 | 7/2007 | Super et al. |
| 2016/0175338 | A1 | 6/2016 | Peabody, III |
| 2018/0312808 | A1 | 11/2018 | Hayday et al. |

FOREIGN PATENT DOCUMENTS

| | | | |
|---|---|---|---|
| CN | 107660151 A | 2/2018 | |
| CN | 110267678 A | 9/2019 | |
| WO | WO 2005012493 | 2/2005 | |
| WO | WO 2007002223 | 1/2007 | |
| WO | WO 2007076950 | 7/2007 | |
| WO | WO-2008/022152 A2 * | 2/2008 | ........... A61K 31/192 |
| WO | WO 2008031056 | 3/2008 | |
| WO | WO 2008150494 | 12/2008 | |
| WO | WO 2009052431 | 4/2009 | |
| WO | WO 2010053716 | 5/2010 | |
| WO | WO 2010095031 | 8/2010 | |
| WO | WO 2011147834 | 12/2011 | |
| WO | WO 2012010561 | 1/2012 | |
| WO | WO 2012010562 | 1/2012 | |
| WO | WO 2012156455 | 2/2012 | |
| WO | WO 2013024095 | 2/2013 | |
| WO | WO 2013024097 | 2/2013 | |
| WO | WO 2015195498 | 12/2015 | |
| WO | WO 2016081518 | 5/2016 | |
| WO | WO 2016189014 | 12/2016 | |
| WO | WO 2016198480 | 12/2016 | |
| WO | WO 2017032679 | 3/2017 | |
| WO | WO 2017072367 | 5/2017 | |
| WO | WO 2017197347 | 11/2017 | |
| WO | WO 2017207574 | 12/2017 | |
| WO | WO 2018002031 | 1/2018 | |
| WO | WO 2018078123 | 5/2018 | |
| WO | WO 2018202808 | 11/2018 | |
| WO | WO 2018220040 | 12/2018 | |
| WO | WO-2019/070424 A1 * | 4/2019 | ............ A61K 35/17 |
| WO | WO 2020055040 | 3/2020 | |
| WO | WO 2020225196 | 11/2020 | |
| WO | WO 2021084062 | 5/2021 | |
| WO | WO 2021084063 | 5/2021 | |
| WO | WO 2021084064 | 5/2021 | |
| WO | WO 2021259902 | 12/2021 | |
| WO | WO 2022117799 | 6/2022 | |
| WO | WO 2023118395 | 6/2023 | |

OTHER PUBLICATIONS

Kantarjian H. et al., Blinatumab versus Chemotherapy for Advanced Acute Lymphoblastic Leukemia, NEJM, 2017.*
Vella et al. (Investig. Clin. Urol. 60:91-98. (2019)) (Year: 2019).*
Cho et al. (Frontiers in Immunology. 9:1-15 (2018)) (Year: 2018).*
Tokuyama et. al. Int. J. Cancer. 122:2526-2534. (2008) (Year: 2008).*
Seidel et. al. Frontiers in Immunology. 5(618):1-12. (2014) (Year: 2014).*
Jurczak et. al. Annals of Oncology. 29:1266-1272 (2018) (Year: 2018).*
Extended European Search Report in EP Application No. 19206479.8 dated May 15, 2020.

(Continued)

*Primary Examiner* — Julie Wu
*Assistant Examiner* — Francesca Edgingtongiordano
(74) *Attorney, Agent, or Firm* — Fish & Richardson P.C.

(57) ABSTRACT

The present disclosure is directed to a combination therapy comprising an anti-CD19 antibody or antibody fragment thereof and gamma delta T-cells (γδ T-cells) for use in the treatment of leukemia or lymphoma.

16 Claims, 4 Drawing Sheets

Specification includes a Sequence Listing.

(56) References Cited

OTHER PUBLICATIONS

Capsomidis et al. "Chimeric Antigen Receptor-Engineered Human Gamma Delta T Cells: Enhanced Cytotoxicity with Retention of Cross Presentation" Molecular Therapy 2018 26(2) :354-365.

Fisher, J. & Anderson, J. "Engineering Approaches in Human Gamma Delta T Cells for Cancer Immunotherapy" Frontiers in Immunology 2018 9:1409 pp. 1-10.

Her et al. "Functional characterization of gamma delta T cells and allogeneic activated NK cells as effector cells for tafasitamab (MOR208) " American Society of Hematology presentation Dec. 9, 2019 Publication No. 3801, Session 605 1 page.

Hoeres et al. "Improving the Efficiency of Vγ9Vδ2 T-Cell Immunotherapy in Cancer" Frontiers in Immunology 2018 9:800 pp. 1-18.

Rischer et al. "Human γδ T cells as mediators of chimaeric-receptor redirected anti-tumour immunity" Journal of Haematology 2004 126:583-592.

Xu et al. "A novel antibody-TCR (AbTCR) platform combines Fab-based antigen recognition with gamma/delta-TCR signaling to facilitate T-cell cytotoxicity with low cytokine release" Cell Discovery 2018 4:62 pp. 1-13.

Almeida et al., "Delta One T Cells for Immunotherapy of Chronic Lymphocytic Leukemia: Clinical-Grade Expansion/Differentiation and Preclinical Proof of Concept," Clinical Cancer Research, 2016, 22(23):5795-5805.

Bird et al., "Single-chain antigen-binding proteins," Science, 1988, 242:423-426.

Deniger et al., "Clinical applications of gamma delta T cells with multivalent immunity," Frontiers in Immunology, 2014, 5:636.

Her et al., "Tafasitamab mediates killing of B-cell non-Hodgkin's lymphoma in combination with γδ T cell or allogeneic NK cell therapy," Cancer Immunology, Immunotherapy, Mar. 29, 2022, 71:2829-2836.

Hollinger and Hudson, "Engineered antibody fragments and the rise of single domains," Nature Biotechnology, 2005, 23:1126-1136.

Huston et al., "Protein engineering of antibody binding sites: recovery of specific activity in an anti-digoxin single-chain Fv analogue produced in *Escherichia coli*," Proc. Natl. Acad. Sci., 1988, 85:5879-5883.

Mordenti et al., "Interspecies scaling of clearance and volume of distribution data for five therapeutic proteins," Pharmaceut. Res., 1991, 8:1351.

PCT International Preliminary Report on Patentability in International Appln. No. PCT/EP2020/080494, dated May 3, 2022, 6 pages.

PCT International Search Report and Written Opinion in International Appln. No. PCT/EP2020/080494, dated Feb. 5, 2021, 11 pages.

Scheuermann et al., "CD19 Antigen in Leukemia and Lymphoma Diagnosis and Immunotherapy," Leukemia and Lymphoma, 1995, 18:385-397.

Ward et al., "Binding activities of a repertoire of single immunoglobulin variable domains secreted from *Escherichia coli*," Nature, 1989, 341:544-546.

Zapata et al., "Engineering linear F(ab')2 fragments for efficient production in *Escherichia coli* and enhanced antiproliferative activity," Protein Eng., 1995, 8:1057-1062.

Her et al., "Functional characterization of gamma delta T cells and allogeneic activated NK cells as effector cells for tafasitamab (MOR208)," Blood, Nov. 13, 2019, 134(Suppln. 1):3801, 3 pages.

Kellner et al., "The Fc-engineered CD19 antibody MOR208 (XmAb5574) induces natural killer cell-mediated lysis of acute lymphoblastic leukemia cells from pediatric and adult patients," Leukemia, Jul. 2013, 27(7):1595-1598.

* cited by examiner

SEQUENCE LISTING

```
<160> NUMBER OF SEQ ID NOS: 13

<210> SEQ ID NO 1
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 1

Ser Tyr Val Met His
1               5


<210> SEQ ID NO 2
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 2

Asn Pro Tyr Asn Asp Gly
1               5


<210> SEQ ID NO 3
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 3

Gly Thr Tyr Tyr Tyr Gly Thr Arg Val Phe Asp Tyr
1               5                   10


<210> SEQ ID NO 4
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
```

Synthetic peptide"

<400> SEQUENCE: 4

Arg Ser Ser Lys Ser Leu Gln Asn Val Asn Gly Asn Thr Tyr Leu Tyr
1 5 10 15

<210> SEQ ID NO 5
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 5

Arg Met Ser Asn Leu Asn Ser
1 5

<210> SEQ ID NO 6
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 6

Met Gln His Leu Glu Tyr Pro Ile Thr
1 5

<210> SEQ ID NO 7
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 7

Glu Val Gln Leu Val Glu Ser Gly Gly Gly Leu Val Lys Pro Gly Gly
1 5 10 15

Ser Leu Lys Leu Ser Cys Ala Ala Ser Gly Tyr Thr Phe Thr Ser Tyr
20 25 30

Val Met His Trp Val Arg Gln Ala Pro Gly Lys Gly Leu Glu Trp Ile
35 40 45

Gly Tyr Ile Asn Pro Tyr Asn Asp Gly Thr Lys Tyr Asn Glu Lys Phe
50 55 60

Gln Gly Arg Val Thr Ile Ser Ser Asp Lys Ser Ile Ser Thr Ala Tyr
65 70 75 80

Met Glu Leu Ser Ser Leu Arg Ser Glu Asp Thr Ala Met Tyr Tyr Cys
85 90 95

Ala Arg Gly Thr Tyr Tyr Tyr Gly Thr Arg Val Phe Asp Tyr Trp Gly
100 105 110

Gln Gly Thr Leu Val Thr Val Ser Ser
115 120

<210> SEQ ID NO 8
<211> LENGTH: 112
<212> TYPE: PRT
<213> ORGANISM: Artificial Sequence
<220> FEATURE:

<221> NAME/KEY: source
<223> OTHER INFORMATION: /note="Description of Artificial Sequence:
Synthetic polypeptide"

<400> SEQUENCE: 8

```
Asp Ile Val Met Thr Gln Ser Pro Ala Thr Leu Ser Leu Ser Pro Gly
1               5                   10                  15

Glu Arg Ala Thr Leu Ser Cys Arg Ser Ser Lys Ser Leu Gln Asn Val
            20                  25                  30

Asn Gly Asn Thr Tyr Leu Tyr Trp Phe Gln Gln Lys Pro Gly Gln Ser
        35                  40                  45

Pro Gln Leu Leu Ile Tyr Arg Met Ser Asn Leu Asn Ser Gly Val Pro
    50                  55                  60

Asp Arg Phe Ser Gly Ser Gly Ser Gly Thr Glu Phe Thr Leu Thr Ile
65                  70                  75                  80

Ser Ser Leu Glu Pro Glu Asp Phe Ala Val Tyr Tyr Cys Met Gln His
                85                  90                  95

Leu Glu Tyr Pro Ile Thr Phe Gly Ala Gly Thr Lys Leu Glu Ile Lys
            100                 105                 110
```

<210> SEQ ID NO 9
<211> LENGTH: 330
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic polypeptide"

<400> SEQUENCE: 9

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Asp Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Gln Phe Asn Trp
145                 150                 155                 160

Tyr Val Asp Gly Val Glu Val His Asn Ala Lys Thr Lys Pro Arg Glu
                165                 170                 175

Glu Gln Phe Asn Ser Thr Phe Arg Val Val Ser Val Leu Thr Val Val
            180                 185                 190

His Gln Asp Trp Leu Asn Gly Lys Glu Tyr Lys Cys Lys Val Ser Asn
        195                 200                 205

Lys Ala Leu Pro Ala Pro Glu Glu Lys Thr Ile Ser Lys Thr Lys Gly
```

```
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Met Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330


<210> SEQ ID NO 10
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 10

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105


<210> SEQ ID NO 11
<211> LENGTH: 451
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 11

Glu Val Gln Leu Val Glu Ser Gly Gly Gly Leu Val Lys Pro Gly Gly
1               5                   10                  15

Ser Leu Lys Leu Ser Cys Ala Ala Ser Gly Tyr Thr Phe Thr Ser Tyr
            20                  25                  30

Val Met His Trp Val Arg Gln Ala Pro Gly Lys Gly Leu Glu Trp Ile
        35                  40                  45

Gly Tyr Ile Asn Pro Tyr Asn Asp Gly Thr Lys Tyr Asn Glu Lys Phe
    50                  55                  60
```

```
Gln Gly Arg Val Thr Ile Ser Ser Asp Lys Ser Ile Ser Thr Ala Tyr
65                  70                  75                  80

Met Glu Leu Ser Ser Leu Arg Ser Glu Asp Thr Ala Met Tyr Tyr Cys
                85                  90                  95

Ala Arg Gly Thr Tyr Tyr Tyr Gly Thr Arg Val Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Asp Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Gln Phe Asn Trp Tyr Val Asp Gly Val Glu Val
        275                 280                 285

His Asn Ala Lys Thr Lys Pro Arg Glu Glu Gln Phe Asn Ser Thr Phe
    290                 295                 300

Arg Val Val Ser Val Leu Thr Val Val His Gln Asp Trp Leu Asn Gly
305                 310                 315                 320

Lys Glu Tyr Lys Cys Lys Val Ser Asn Lys Ala Leu Pro Ala Pro Glu
                325                 330                 335

Glu Lys Thr Ile Ser Lys Thr Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Met Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450
```

<210> SEQ ID NO 12
<211> LENGTH: 219

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 12

Asp Ile Val Met Thr Gln Ser Pro Ala Thr Leu Ser Leu Ser Pro Gly
1               5                   10                  15

Glu Arg Ala Thr Leu Ser Cys Arg Ser Ser Lys Ser Leu Gln Asn Val
            20                  25                  30

Asn Gly Asn Thr Tyr Leu Tyr Trp Phe Gln Gln Lys Pro Gly Gln Ser
        35                  40                  45

Pro Gln Leu Leu Ile Tyr Arg Met Ser Asn Leu Asn Ser Gly Val Pro
    50                  55                  60

Asp Arg Phe Ser Gly Ser Gly Ser Gly Thr Glu Phe Thr Leu Thr Ile
65                  70                  75                  80

Ser Ser Leu Glu Pro Glu Asp Phe Ala Val Tyr Tyr Cys Met Gln His
                85                  90                  95

Leu Glu Tyr Pro Ile Thr Phe Gly Ala Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215


<210> SEQ ID NO 13
<211> LENGTH: 556
<212> TYPE: PRT
<213> ORGANISM: Homo sapiens

<400> SEQUENCE: 13

Met Pro Pro Pro Arg Leu Leu Phe Phe Leu Leu Phe Leu Thr Pro Met
1               5                   10                  15

Glu Val Arg Pro Glu Glu Pro Leu Val Val Lys Val Glu Glu Gly Asp
            20                  25                  30

Asn Ala Val Leu Gln Cys Leu Lys Gly Thr Ser Asp Gly Pro Thr Gln
        35                  40                  45

Gln Leu Thr Trp Ser Arg Glu Ser Pro Leu Lys Pro Phe Leu Lys Leu
    50                  55                  60

Ser Leu Gly Leu Pro Gly Leu Gly Ile His Met Arg Pro Leu Ala Ile
65                  70                  75                  80

Trp Leu Phe Ile Phe Asn Val Ser Gln Gln Met Gly Gly Phe Tyr Leu
                85                  90                  95

Cys Gln Pro Gly Pro Pro Ser Glu Lys Ala Trp Gln Pro Gly Trp Thr
            100                 105                 110
```

-continued

```
Val Asn Val Glu Gly Ser Gly Glu Leu Phe Arg Trp Asn Val Ser Asp
        115                 120                 125

Leu Gly Gly Leu Gly Cys Gly Leu Lys Asn Arg Ser Ser Glu Gly Pro
    130                 135                 140

Ser Ser Pro Ser Gly Lys Leu Met Ser Pro Lys Leu Tyr Val Trp Ala
145                 150                 155                 160

Lys Asp Arg Pro Glu Ile Trp Glu Gly Glu Pro Pro Cys Leu Pro Pro
                165                 170                 175

Arg Asp Ser Leu Asn Gln Ser Leu Ser Gln Asp Leu Thr Met Ala Pro
            180                 185                 190

Gly Ser Thr Leu Trp Leu Ser Cys Gly Val Pro Pro Asp Ser Val Ser
        195                 200                 205

Arg Gly Pro Leu Ser Trp Thr His Val His Pro Lys Gly Pro Lys Ser
    210                 215                 220

Leu Leu Ser Leu Glu Leu Lys Asp Asp Arg Pro Ala Arg Asp Met Trp
225                 230                 235                 240

Val Met Glu Thr Gly Leu Leu Leu Pro Arg Ala Thr Ala Gln Asp Ala
                245                 250                 255

Gly Lys Tyr Tyr Cys His Arg Gly Asn Leu Thr Met Ser Phe His Leu
            260                 265                 270

Glu Ile Thr Ala Arg Pro Val Leu Trp His Trp Leu Leu Arg Thr Gly
        275                 280                 285

Gly Trp Lys Val Ser Ala Val Thr Leu Ala Tyr Leu Ile Phe Cys Leu
    290                 295                 300

Cys Ser Leu Val Gly Ile Leu His Leu Gln Arg Ala Leu Val Leu Arg
305                 310                 315                 320

Arg Lys Arg Lys Arg Met Thr Asp Pro Thr Arg Arg Phe Phe Lys Val
                325                 330                 335

Thr Pro Pro Pro Gly Ser Gly Pro Gln Asn Gln Tyr Gly Asn Val Leu
            340                 345                 350

Ser Leu Pro Thr Pro Thr Ser Gly Leu Gly Arg Ala Gln Arg Trp Ala
        355                 360                 365

Ala Gly Leu Gly Gly Thr Ala Pro Ser Tyr Gly Asn Pro Ser Ser Asp
    370                 375                 380

Val Gln Ala Asp Gly Ala Leu Gly Ser Arg Ser Pro Pro Gly Val Gly
385                 390                 395                 400

Pro Glu Glu Glu Glu Gly Glu Gly Tyr Glu Glu Pro Asp Ser Glu Glu
                405                 410                 415

Asp Ser Glu Phe Tyr Glu Asn Asp Ser Asn Leu Gly Gln Asp Gln Leu
            420                 425                 430

Ser Gln Asp Gly Ser Gly Tyr Glu Asn Pro Glu Asp Glu Pro Leu Gly
        435                 440                 445

Pro Glu Asp Glu Asp Ser Phe Ser Asn Ala Glu Ser Tyr Glu Asn Glu
    450                 455                 460

Asp Glu Glu Leu Thr Gln Pro Val Ala Arg Thr Met Asp Phe Leu Ser
465                 470                 475                 480

Pro His Gly Ser Ala Trp Asp Pro Ser Arg Glu Ala Thr Ser Leu Gly
                485                 490                 495

Ser Gln Ser Tyr Glu Asp Met Arg Gly Ile Leu Tyr Ala Ala Pro Gln
            500                 505                 510

Leu Arg Ser Ile Arg Gly Gln Pro Gly Pro Asn His Glu Glu Asp Ala
        515                 520                 525
```

-continued

```
Asp Ser Tyr Glu Asn Met Asp Asn Pro Asp Gly Pro Asp Pro Ala Trp
    530                 535                 540

Gly Gly Gly Gly Arg Met Gly Thr Trp Ser Thr Arg
545                 550                 555
```

ANTI-TUMOR COMBINATION THERAPY COMPRISING ANTI-CD19 ANTIBODY AND GAMMA DELTA T-CELLS

This patent application claims the benefit of priority from EP 19206479.8 filed Oct. 31, 2019, teachings of which are herein incorporated by reference in their entirety.

FIELD OF THE INVENTION

The present disclosure is directed to a combination therapy comprising an anti-CD19 antibody or antibody fragment thereof and gamma delta T-cells (γδ T-cells) for use in the treatment of leukemia or lymphoma.

BACKGROUND

CD19 is a 95-kDa transmembrane glycoprotein of the immunoglobulin superfamily containing two extracellular immunoglobulin-like domains and an extensive cytoplasmic tail. The protein is a pan-B lymphocyte surface receptor and is ubiquitously expressed from the earliest stages of pre-B cell development onwards until it is down-regulated during terminal differentiation into plasma cells. It is B-lymphocyte lineage specific and not expressed on hematopoietic stem cells and other immune cells, except some follicular dendritic cells. CD19 functions as a positive regulator of B cell receptor (BCR) signalling and is important for B cell activation and proliferation and in the development of humoral immune responses. It acts as a co-stimulatory molecule in conjunction with CD21 and CD81 and is critical for B cell responses to T-cell-dependent antigens. The cytoplasmic tail of CD19 is physically associated with a family of tyrosine kinases that trigger downstream signalling pathways via the src-family of protein tyrosine kinases. CD19 is an attractive target for cancers of lymphoid origin since it is highly expressed in nearly ail-chronic lymphocytic leukemia (CLL) and non-Hodgkin's lymphomas (NHL), as well as many other different types of leukemias, including acute lymphocytic leukemia (ALL) and hairy cell leukemia (HCL).

Tafasitamab (former names: MOR00208 and XmAb®5574) is a humanized monoclonal antibody that targets the antigen CD19, a transmembrane protein involved in B-cell receptor signalling. Tafasitamab has been engineered in the IgG Fc-region to enhance antibody-dependent cell-mediated cytotoxicity (ADCC), thus improving a key mechanism for tumor cell killing and offering potential for enhanced efficacy compared to conventional antibodies, i.e. non-enhanced antibodies. Tafasitamab has or is currently being studied in several clinical trials, such as in CLL, ALL and NHL. In some of those trials, Tafasitamab is used in combination with Idelalisib, Lenalidomide or Venetoclax.

Despite recent discoveries and developments of several anti-cancer agents, due to poor prognosis for many types of cancers including CD19-expressing tumors, there is still a need for an improved method or therapeutic agent for treating such types of cancers. Accordingly, the present inventors have confirmed that combined administration of γδ T-cells and an antibody or antibody fragment specific for CD19 has superior effects on the treatment of malignant lymphomas of B cell origin, and have completed the present invention.

SUMMARY OF INVENTION

The present disclosure provides a novel combination for use in the treatment of cancer, comprising an antibody or antibody fragment specific for CD19 and γδ T-cells.

Since their discovery in the 1980s, it has been meanwhile acknowledged that γδ T-cells are important players in infections and also malignancies such as cancer. Activated γδ T-cells have powerful cytotoxic and broad tumor recognition abilities independent of major histocompatibility complex (MHC) molecules being present on their target cells, in addition, γ5 T-cells were shown to be potent mediators of antibody dependent cell-mediated cytotoxicity (ADCC). As of today, it was shown that the anti-tumor effect of γδ T-cells can be reinforced substantially by anti-CD20 antibodies (Tokuyama et al. 2008; Hoeres et al. 2018). Moreover, the Fc-enhanced anti-CD20 antibody Obinutuzumab shows increased tumor cell killing compared to non-Fc-enhanced antibodies like Rituximab when combined with γδ T-cells. However, tumor cell killing activity of antibodies specific for other surface antigens than CD20 in the presence of γδ T-cells was not yet evaluated. Hence the object of the present disclosure is to provide an alternative combined therapy that comprises an antibody and γδ T-cells.

In order to achieve the above object, the present disclosure provides a combination for use in the treatment of cancer, comprising an antibody or antibody fragment specific for CD19 and γδ T-cells.

In the present disclosure the inventors have combined γδ T-cells with the CD19-targeting antibodies Tafasitamab (Fc-enhanced) and Xmab5603 (non-Fc-enhanced) and evaluated their anti-tumor activity in patient derived CLL, MCL and B-ALL samples as well as various lymphoma and leukemia cell lines in ADCC assays. Altogether, an increased rate of cell lysis when γδ T-cells were combined with the Fc-enhanced anti-CD19 antibody Tafasitamab in comparison to the non-Fc-enhanced Xmab5603 or a negative control IgG1 antibody was observed.

In summary, it is shown that γδ T-cells are a potential effector cell population in antibody based tumor therapy as demonstrated for the Fc-enhanced CD19-targeting antibody Tafasitamab in this study. Tafasitamab showed strong anti-tumor activity mediated by γδ T-cells towards several lymphoma and leukemia cell lines as well as primary patient-derived CLL, MCL and BALL cells and may hold a promising approach for lymphoma and leukemia therapy.

The γδ T-cells can be derived from any suitable autologous or allogeneic γδ T-cell or population thereof. In some embodiments, suitable γδ T-cells for use as a source for the presently described γδ T-cells include Vδ1 cells, Vδ2 cells, Vδ3 cells, Vδ5 cells, and Vδ8 cells. For example, provided herein are methods for separating and expanding Vδ1 cells from a non-haematopoietic tissue, such as skin or gut. For example, Vδ1 cells can be isolated from human skin biopsies as described in US2018/0312808, which is hereby incorporated by reference in its entirety and specifically for methods of isolating Vδ1 cells from tissue.

In other embodiments, suitable γδ T-cells can be derived from blood (e.g., peripheral blood). Methods of isolating and expanding Vδ1 cells from blood include those described, for example, in U.S. Pat. No. 9,499,788 and International Patent Publication No. WO2016/198480, each of which is incorporated herein by reference in its entirety. Also Vγ9Vδ2 T-cells can be isolated from peripheral blood and further cultivated ex vivo. Cultivation of Vγ9Vδ2 T-cells can be optimized in the presence of IL-2 and zoledronic acid (ZOL). Methods of isolating and expanding Vγ9Vδ2 T-cells from blood include those described, for example in Hoeres et al. 2018.

In some embodiments, suitable γδ T-ceils can be derived from tumor tissue (e.g., tumor-infiltrating γδ T-cells). Alternatively, suitable γδ T-cells that can be engineered to express a heterologous targeting construct can be derived from non-haematopoietic tissue according to methods described below. These cells can be cultured in the presence of one or more factors (e.g., TCR agonists, co-receptor agonists, and/or cytokines, e.g., IL-4, IL-15, and/or IFN-g) in gas-permeable bioreactor bags for up to 21 days or more. Variations of this method, and other methods of obtaining Vδ1 T cells are suitable as part of the present invention. For example, blood-derived Vδ1 T cells can alternatively be obtained using methods described, for example, in International Patent Publications WO2017/197347 and WO2016/081518 (US Publ. No. 2016/0175338), each of which is incorporated herein by reference in its entirety.

The present disclosure provides a pharmaceutical combination, comprising an antibody or antibody fragment specific for CD19 and gamma delta T-ceils (γδ T-cell) for use in the treatment of cancer.

In one aspect the present disclosure provides a pharmaceutical combination, comprising an antibody or antibody fragment specific for CD19 and gamma delta T-cells (γδ T-cell) for use in the treatment of cancer wherein the antibody comprises a heavy chain variable region comprising an HCDR1 region comprising the sequence SYVMH (SEQ ID NO: 1), an HCDR2 region comprising the sequence NPYNDG (SEQ ID NO: 2), and an HCDR3 region comprising the sequence GTYYYGTRVFDY (SEQ ID NO: 3) and a light chain variable region comprising comprising the sequence LCDR1 region comprising the sequence RSSKSLQNVNGNTYLY (SEQ ID NO: 4), an LCDR2 region comprising the sequence RMSNLNS (SEQ ID NO: 5), and an LCDR3 region comprising the sequence MQHLEYPIT (SEQ ID NO: 6) for use in the treatment of cancer.

In one aspect the present disclosure provides a pharmaceutical combination, comprising an antibody or antibody fragment specific for CD19 and gamma delta T-cells (γδ T-cell) for use in the treatment of cancer wherein the antibody comprises a heavy chain variable region comprising an HCDR1 region of SYVMH (SEQ ID NO: 1), an HCDR2 region of NPYNDG (SEQ ID NO: 2), and an HCDR3 region of GTYYYGTRVFDY (SEQ ID NO: 3) and a light chain variable region comprising an LCDR1 region of RSSKSLQNVNGNTYLY (SEQ ID NO: 4), an LCDR2 region of RMSNLNS (SEQ ID NO: 5), and an LCDR3 region of MQHLEYPIT (SEQ ID NO: 6) for use in the treatment of cancer.

In another aspect the antibody or antibody fragment specific for CD19 comprises a heavy chain variable region of (SEQ ID NO: 7)
EVQLVESGGGLVKPGGSLKLSCAASGYTFTSYVMHWVRQAPGKGLEWI
GYINPYNDGTKYNEKFQGRVTISSDKSISTAYMELSSLRSEDTAMYYC
ARGTYYYGTRVFDYWGQGTLVTVSS and a light chain variable region of (SEQ ID NO: 8)
DIVMTQSPATLSLSPGERATLSCRSSKSLQNVNGNTYLYWFQQKPGQS
PQLLIYRMSNLNSGVPDRFSGSGSGTEFTLTISSLEPEDFAVYYCMQH
LEYPITFGAGTKLEIK.

In another aspect the antibody or antibody fragment specific for CD19 has effector function. In another aspect the antibody or antibody fragment specific for CD19 has an enhanced effector function. In one embodiment the effector function is ADCC. In one embodiment the antibody or antibody fragment specific for CD19 has an enhanced ADCC activity. In a further embodiment the antibody or antibody fragment specific for CD19 comprises an Fc domain comprising an amino acid substitution at position S239 and/or I332, wherein the numbering is according to the EU index as in Kabat.

In yet another aspect the antibody or antibody fragment specific for CD19 comprises a heavy chain constant region of (SEQ ID NO: 9)
ASTKGPSVFPLAPSSKSTSGGTAALGCLVKDYFPEPVTVSWNSGALTS
GVHTFPAVLQSSGLYSLSSVVTVPSSSLGTQTYICNVNFIKPSNTKVD
KKVEIDKSCDKTHTCPPCPAPELLGGPDVFLFPPKPKDTLMISRTPEV
TCVVVDVSHEDPEVQFNWYVDGVEVFINAKTKPREEQFNSTFRVVSVL
IVVHQDWLNGKEYKCKVSNKALPAPEEKTISKTKGQPREPQVYTLPPS
REEMTKNQVSLICLVKGFYPSDIAVEWESNGQPENNYKTTPPMLDSDG
SFFLYSKLTVDKSRWQQGNVFSCSVMHEALHNHYTQKSLSLSPGK.

In a further aspect the antibody specific for CD19 comprises a light chain constant region of (SEQ ID NO: 10)
RTVAAPSVFIFPPSDEQLKSGTASVVCLLNNFYPREAKVQWKVDNALQ
SGNSQESVTEQDSKDSTYSLSSIITLSKADYEKHKVYACEVTHQGLSS
PVTKSFNRGEC.

In yet another aspect the antibody specific for CD19 comprises a heavy chain constant region of (SEQ ID NO: 9)
ASTKGPSVFPLAPSSKSTSGGTAALGCLVKDYFPEPVTVSWNSGALTS
GVHTFPAVLQSSGLYSLSSVVIVPSSSLGTQTYICNVNHKPSNTKVDK
KVEPKSCDKTHTCPPCPAPELLGGPDVFLFPPKPKDTLMISRTPEVTC
VVVDVSHEDPEVQFNWYVDGVEVHNAKTKPREEQFNSTFRVVSVLTVV
HQDWLNGKEYKCKVSNKALPAPEEKTISKTKGQPREPQVYTLPPSREE
MTKNQVSLICLVKGFYPSDIAVEWESNGQPENNYKTTPPMLDSDGSFF
LYSKLIVDKSRWQQGNVFSCSVMHEALHNHYTQKSLSLSPGK and a light chain constant region of (SEQ ID NO: 10)
RTVAAPSVFIFPPSDEQLKSGTASVVCLINNFYPREAKVQWKVDNALQ
SGNSQESVTEQDSKDSTYSLSSTLTLSKADYEKHKVYACEVTHQGLSS
PVTKSFNRGEC.

In yet another aspect the antibody specific for CD19 comprises a heavy chain region of (SEQ ID NO: 11)
EVQLVESGGGLVKPGGSLKLSCAASGYTFTSYVMHWVRQAPGKGLEWI
GYINPYNDGTKYNEKFQGRVTISSDKSISTAYMELSSLRSEDTAMYYC -continued

```
ARGTYYYGTRVFDYWGQGTLVTVSSASTKGPSVFPLAPSSKSTSGGTA

ALGCLVKDYFPEPVTVSWNSGALTSGVHTFPAVLQSSGLYSLSSVVIV

PSSSLGTQTYECNVNHKPSNTKVDKKVEPKSCDKTHTCPPCPAPELLG

GPDVFLFPPKPKDTLMISRIPEVICVVVDVSHEDPEVQFNWYVDGVEV

HNAKTKPREEQFNSTFRVVSVLTVVHQDWLNGKEYKCKVSNKALPAPE

EKTISKTKGQPREPQVYTLPPSREEMTKNQVSLTCLVKGFYPSDIAVE

WESNGQPENNYKTTPPMLDSDGSFFLYSKLTVDKSRWQQGNVFSCSVM

HEALHNHYTQKSLSLSPGK
```

and a light chain region of

```
                                            (SEQ ID NO: 12)
DIVMTQSPATLSLSPGERATLSCRSSKSLQNVNGNTYLYVVFQQKPGQ

SPQLLIYRMSNLNSGVPDRFSGSGSGTEFTLTISSLEPEDFAVYYCMQ

HLEYPITFGAGTKLEIKRTVAAPSVFIFPPSDEQLKSGTASVVCLLNN

FYPREAKVQWKVDNALQSGNSQESVTEQDSKDSTYSLSSTLTLSKADY

EKHKVYACEVTHQGLSSPVTKSFNRGEC.
```

In one aspect the present disclosure provides a pharmaceutical combination, comprising an antibody specific for CD19 and gamma delta T-cells (γδ T-cell) for use in the treatment of cancer wherein the γδ T-cells comprise an enriched γδ T-cell population. In one embodiment the enriched γδ T-cell population comprises non-engineered or engineered γδ T-cells and/or admixtures thereof. In a further embodiment the present disclosure provides a pharmaceutical combination, comprising an antibody specific for CD19 and an enriched γδ T-cell population for use in the treatment of cancer.

In another aspect the present disclosure provides a pharmaceutical combination, comprising an antibody specific for CD19 and gamma delta T-cells (γδ T-cell) for use in the treatment of cancer wherein the γδ T-cells comprise non-engineered or engineered γδ T-cells and/or admixtures thereof. In another embodiment the γδ T-cells are a population of non-engineered γδ T-cells. In yet another embodiment the γδ T-cells are a population of engineered γδ T-cells.

In one aspect the present disclosure provides a pharmaceutical combination, comprising an antibody specific for CD19 and gamma delta T-cells (γδ T-cell) for use in the treatment of cancer wherein the γδ T-cells are isolated from peripheral blood, tumor tissue or non-hematopoietic tissue, in one embodiment the γδ T-cells are isolated from peripheral blood. In another embodiment the γδ T-cells are a population of γδ T-cells isolated from peripheral blood. In another embodiment the γδ T-cells are a population of Vγ9Vδ2 T-cells isolated from peripheral blood. In further embodiment the γδ T-cells are a population of Vγ9Vδ2 T-cells isolated from peripheral blood wherein the Vγ9Vδ2 T-cells were cultivated ex vivo in the presence of IL-1 and zoledronic acid (ZOL).

In one aspect the present disclosure provides a pharmaceutical combination, comprising an antibody specific for CD19 and gamma delta T-cells (γδ T-cell) for use in the treatment of cancer wherein the cancer is a hematological cancer. In one embodiment the hematological cancer is chronic lymphocytic leukemia (CLL), non-Hodgkin's lymphoma (NHL), small lymphocytic lymphoma (SLL) or acute lymphoblastic leukemia (ALL). In another embodiment the hematological cancer is non-Hodgkin's lymphoma (NHL). In a further embodiment the non-Hodgkin's lymphoma is selected from the group consisting of follicular lymphoma, small lymphocytic lymphoma, mucosa-associated lymphoid tissue, marginal zone lymphoma, diffuse large B cell lymphoma, Burkitt's lymphoma and mantle cell lymphoma.

In one aspect the present disclosure provides a pharmaceutical combination, comprising an antibody specific for CD19 and gamma delta T-cells (γδ T-cell) for use in the treatment of cancer, wherein the antibody specific for CD19 and the γδ T-cells are administered in a separate manner.

In one aspect the present disclosure provides a pharmaceutical combination, comprising an antibody specific for CD19 and gamma delta T-cells (γδ T-cell) for use in the treatment of cancer, wherein the antibody specific for CD19 and the γδ T-cells are administered in a simultaneous manner.

In one aspect the present disclosure provides kit for use in the treatment of cancer comprising an antibody specific for CD19 and gamma delta T-cells (γδ T-cell).

DEFINITIONS

Figure 1:
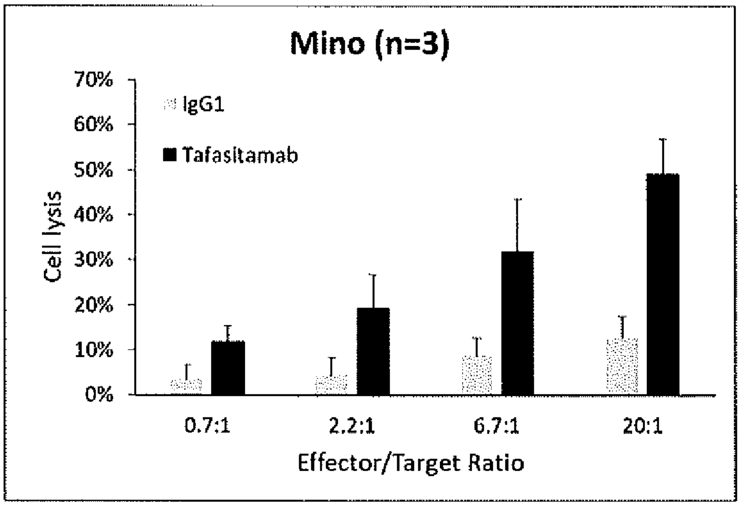
FIG. 1: Representative ADCC assays of MOR00208 at increasing effector to target cell (E:T) ratios. Results for specific cell killing expressed as % dead target cells mediated by MOR00208 (black) or the IgG1 negative control (white) and γδ T-ceils from healthy donors are depicted for three target cell lines Mino, Daudi and Jeko. Four different E:T ratios between 0.7:1 and 20:1 were tested.
Figure 1:
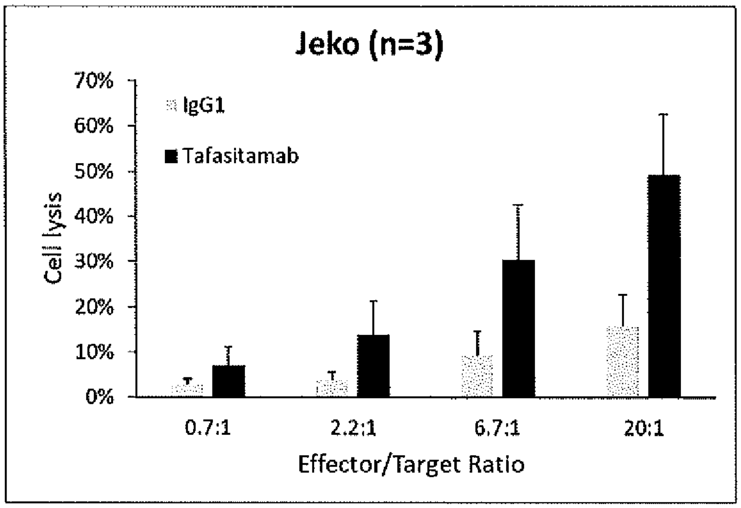

The term "CD19" refers to the protein known as CD19, having the following synonyms: B4, B-lymphocyte antigen CD19, B-lymphocyte surface antigen B4, CVID3, Differentiation antigen CD19, MGC12802, and T-cell surface antigen Leu-12.

Human CD19 has the amino acid sequence of:

```
                                     (SEQ ID NO: 13)
MPPPRLLFFLLFLIPMEVRPEEPLVVKVEEGDNAVLQCLKGTSDGPTQ

QLTWSRESPLKPFLKLSLGLPGLGIHMRPLAIWLFIFNVSQQMGGFYL

CQPGPPSEKAWQPGWTVNVEGSGELFRWNVSDLGGLGCGLKNRSSEGP

SSPSGKLMSPKLYVWAKDRPEIWEGEPPCLPPRDSLNQSLSQDLTMAP

GSTLWLSCGVPPDSVSRGPLSWTHVHPKGPKSLLSLELKDDRPARDMW

VMETGLLLPRATAQDAGKYYCHRGNLIMSFHLEITARPVLINHWLLRT

GGWKVSAVTLAYLIFCLCSLVGILHLQRALVLRRKRKRMTDPTRRFFK

VTPPPGSGPQNQYGNVLSLPTPTSGLGRAQRWAAGLGGTAPSYGNPSS

DVQADGALGSRSPPGVGPEEEEGEGYEEPDSEEDSEFYENDSNLGQDQ

LSQDGSGYENPEDEPLGPEDEDSFSNAESYENEDEELTQPVARTMDFL

SPHGSAWDPSREATSLGSQSYEDMRGILYAAPQLRSIRGQPGPNHEED

ADSYENMDNPDGPDPAWGGGGRMGTWSTR.
```

"MOR00208" and "XmAb 5574" and "tafasitamab" are used as synonyms for the anti-CD19 antibody according to Table 1. Table 1 provides the amino acid sequences of MOR00208/tafasitamb. The MOR00208 antibody is described in U.S. patent application Ser. No. 12/377,251, which is incorporated by reference in its entirety. U.S. patent application Ser. No. 12/377,251 describes the antibody named 4G7 H1.52 Hybrid S239D/I332E/4G7 L1.155 (later named MOR00208 and tafasitamab).

The term "antibody" as used herein refers to a protein comprising at least two heavy (H) chains and two light (L) chains inter-connected by disulfide bonds, which interacts with an antigen. Each heavy chain is comprised of a variable heavy chain region (abbreviated herein as VH) and a heavy chain constant region. The heavy chain constant region is comprised of three domains, CH1, CH2 and CH3. Each light chain is comprised of a variable light chain region (abbreviated herein as VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FR's arranged from amino-terminus to carboxy-terminus in the following order: FR1, CDR1, FR2, CDR2, FR3, CDR3, and FR4. The variable regions of the heavy and light chains contain a binding domain that interacts with an antigen. The term "antibody" includes for example, monoclonal antibodies, human antibodies, humanized antibodies, camelised antibodies and chimeric antibodies. The antibodies can be of any isotype (e.g., IgG, IgE, IgM, IgD, IgA and IgY), class (e.g., IgG1, IgG2, IgG3, IgG4, IgA1 and IgA2) or subclass. Both the light and heavy chains are divided into regions of structural and functional homology.

The phrase "antibody fragment", as used herein, refers to one or more portions of an antibody that retain the ability to specifically interact with (e.g., by binding, steric hindrance, stabilizing spatial distribution) an antigen. Examples of binding fragments include, but are not limited to, a Fab fragment, a monovalent fragment consisting of the VL, VH, CL and CH1 domains; a F(ab)2 fragment, a bivalent fragment comprising two Fab fragments linked by a disulfide bridge at the hinge region; a Fd fragment consisting of the VH and CH1 domains; a Fv fragment consisting of the VL and VH domains of a single arm of an antibody; a dAb fragment (Ward et al., (1989) Nature 341:544-546), which consists of a VH domain; and an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al., (1988) Science 242:423-426; and Huston et al., (1988) Proc. Natl. Acad. Sci. 85:5879-5883). Such single chain antibodies are also intended to be encompassed within the term "antibody fragment". These antibody fragments are obtained using conventional techniques known to those of skill in the art, and the fragments are screened for utility in the same manner as are intact antibodies. Antibody fragments can also be incorporated into single domain antibodies, maxibodies, minibodies, intrabodies, diabodies, triabodies, tetrabodies, v-NAR and bis-scFv (see, e.g., Hollinger and Hudson, (2005) Nature Biotechnology 23:1126-1136). Antibody fragments can be grafted into scaffolds based on polypeptides such as Fibronectin type III (Fn3) (see U.S. Pat. No. 6,703,199, which describes fibronectin polypeptide monobodies). Antibody fragments can be incorporated into single chain molecules comprising a pair of tandem Fv segments (VH-CH1-VH-CH1) which, together with complementary light chain polypeptides, form a pair of antigen-binding sites (Zapata et al., (1995) Protein Eng. 8:1057-1062; and U.S. Pat. No. 5,641,870).

"Administered" or "administration" includes but is not limited to delivery of a drug by an injectable form, such as, for example, an intravenous, intramuscular, intradermal or subcutaneous route or mucosal route, for example, as a nasal spray or aerosol for inhalation or as an ingestible solution, capsule or tablet. Preferably, the administration is by an injectable form.

The term "effector function" refers to those biological activities attributable to the Fc region of an antibody, which vary with the antibody isotype. Non-limiting examples of antibody effector functions include C1q binding and complement dependent cytotoxicity (CDC); Fc receptor binding and antibody-dependent cell-mediated cytotoxicity (ADCC) and/or antibody-dependent cellular phagocytosis (ADCP); down regulation of cell surface receptors (e.g. B cell receptor); and B cell activation.

"Antibody-dependent cell-mediated cytotoxicity" or "ADCC" refers to a form of cytotoxicity in which antibodies bound onto Fc receptors (FcRs) present on certain cytotoxic cells (e.g. NK cells, neutrophils, and macrophages) enable these cytotoxic effector cells to bind specifically to an antigen-bearing target cell and subsequently kill the target cell with cytotoxins. The primary cells for mediating ADCC, NK cells, express FcγRIII only, whereas monocytes express FcγRI, FcγRII, and FcγRIII.

"Complement-dependent cytotoxicity" or "CDC" refers to the lysis of a target cell in the presence of complement. Activation of the classical complement pathway is initiated by the binding of the first component of the complement system (C1q) to antibodies (of the appropriate subclass) of the present disclosure, which are bound to their cognate antigen.

"Antibody-dependent cellular phagocytosis" or "ADCP" refers to a mechanism of elimination of antibody-coated target cells by internalization by phagocytic cells, such as macrophages or dendritic cells.

The term "hematologic cancer" includes blood-borne tumors and diseases or disorders involving abnormal cell growth and/or proliferation in tissues of hematopoietic origin, such as lymphomas, leukemias, and myelomas.

Non-Hodgkin's lymphoma ("NHL") is a heterogeneous malignancy originating from lymphocytes. In the United States (U.S.), the incidence is estimated at 65,000/year with mortality of approximately 20,000 (American Cancer Society, 2006; and SEER Cancer Statistics Review). The disease can occur in all ages, the usual onset begins in adults over 40 years, with the incidence increasing with age. NHL is characterized by a clonal proliferation of lymphocytes that accumulate in the lymph nodes, blood, bone marrow and spleen, although any major organ may be involved. The current classification system used by pathologists and clinicians is the World Health Organization (WHO) Classification of Tumours, which organizes NHL into precursor and mature B-cell or T-cell neoplasms. The PDQ is currently dividing NHL as indolent or aggressive for entry into clinical trials. The indolent NHL group is comprised primarily of follicular subtypes, small lymphocytic lymphoma, MALT (mucosa-associated lymphoid tissue), and marginal zone; indolent encompasses approximately 50% of newly diagnosed B-cell NHL patients. Aggressive NHL includes patients with histologic diagnoses of primarily diffuse large B cell (DLBL, "DLBCL", or DLCL) (40% of all newly diagnosed patients have diffuse large cell), Burkitt's, and mantle cell ("MCL"). The clinical course of NHL is highly variable. A major determinant of clinical course is the histologic subtype. Most indolent types of NHL are considered to be incurable disease. Patients respond initially to either chemotherapy or antibody therapy and most will relapse. Studies to date have not demonstrated an improvement in survival with early intervention. In asymptomatic patients, it is acceptable to "watch and wait" until the patient becomes symptomatic or the disease pace appears to be accelerating. Over time, the disease may transform to a more aggressive histology. The median survival is 8 to 10 years, and indolent patients often receive 3 or more treatments during the treatment phase of their disease. Initial treatment of the symptomatic indolent NHL patient historically has been combination chemotherapy. The most commonly used agents include: cyclophosphamide, vincristine and prednisone (CVP); or cyclophosphamide, adriamycin, vincristine, prednisone (CHOP). Approximately 70% to 80% of patients will respond to their initial chemotherapy, duration of remissions last on the order of 2-3 years. Ultimately the majority of patients relapse. The discovery and clinical use of the anti-CD20 antibody, rituximab, has provided significant improvements in response and survival rate. The current standard of care for most patients is rituximab+CHOP (R-CHOP) or rituximab+CVP (R-CVP). Rituximab therapy has been shown to be efficacious in several types of NHL, and is currently approved as a first line treatment for both indolent (follicular lymphoma) and aggressive NHL (diffuse large B cell lymphoma). However, there are significant limitations of anti-CD20 monoclonal antibody (mAb), including primary resistance (50% response in relapsed indolent patients), acquired resistance (50% response rate upon re-treatment), rare complete response (2% complete response rate in relapsed population), and a continued pattern of relapse. Finally, many B cells do not express CD20, and thus many B-cell disorders are not treatable using anti-CD20 antibody therapy.

In addition to NHL there are several types of leukemias that result from dysregulation of B ceils. Chronic lymphocytic leukemia (also known as "chronic lymphoid leukemia" or "CLL"), is a type of adult leukemia caused by an abnormal accumulation of B lymphocytes. In CLL, the malignant lymphocytes may look normal and mature, but they are not able to cope effectively with infection. CLL is the most common form of leukemia in adults. Men are twice as likely to develop CLL as women. However, the key risk factor is age. Over 75% of new cases are diagnosed in patients over age 50. More than 10,000 cases are diagnosed every year and the mortality is almost 5,000 a year (American Cancer Society, 2006; and SEER Cancer Statistics Review). CLL is an incurable disease but progresses slowly in most cases. Many people with CLL lead normal and active lives for many years. Because of its slow onset, early-stage CLL is generally not treated since it is believed that early CLL intervention does not improve survival time or quality of life. Instead, the condition is monitored over time. Initial CLL treatments vary depending on the exact diagnosis and the progression of the disease. There are dozens of agents used for CLL therapy. Combination chemotherapy regimens such as FCR (fludarabine, cyclophosphamide and rituximab), and BR (Ibrutinib and rituximab) are effective in both newly-diagnosed and relapsed CLL. Allogeneic bone marrow (stem cell) transplantation is rarely used as a first-line treatment for CLL due to its risk.

Another type of leukemia is Small lymphocytic lymphoma ("SLL") that is considered a CLL variant that lacks the clonal lymphocytosis required for the CLL diagnosis, but otherwise shares pathological and immunophenotypic features (Campo et al., 2011), The definition of SLL requires the presence of lymphadenopathy and/or splenomegaly. Moreover, the number of B lymphocytes in the peripheral blood should not exceed 5×109/L. In SLL, the diagnosis should be confirmed by histopathologic evaluation of a lymph node biopsy whenever possible (Hallek et al., 2008). The incidence of SLL is approximately 25% of CLL in the US (Dores et al., 2007).

Another type of leukemia is acute lymphoblastic leukemia (ALL), also known as acute lymphocytic leukemia. ALL is characterized by the overproduction and continuous multiplication of malignant and immature white blood cells (also known as lymphoblasts) in the bone marrow. 'Acute' refers to the undifferentiated, immature state of the circulating lymphocytes ("blasts"), and that the disease progresses rapidly with life expectancy of weeks to months if left untreated. ALL is most common in childhood with a peak incidence of 4-5 years of age. Children of age 12-16 die more easily from it than others. Currently, at least 80% of childhood ALL are considered curable. Under 4,000 cases are diagnosed every year and the mortality is almost 1,500 a year (American Cancer Society, 2006; and SEER Cancer Statistics Review).

"Subject" or "patient" as used in this context refers to any mammal, including rodents, such as mouse or rat, and primates, such as cynomolgus monkey (*Macaca fascicularis*), rhesus monkey (*Macaca mulatta*) or humans (*Homo sapiens*). Preferably, the subject or patient is a primate, most preferably a human patient, even more preferably an adult human patient.

The terms "engineered" or "modified" as used herein includes manipulation of nucleic acids or polypeptides by synthetic means (e.g. by recombinant techniques, in vitro peptide synthesis, by enzymatic or chemical coupling of peptides or some combination of these techniques). Preferably, the antibodies or antibody fragments according to the present disclosure are engineered or modified to improve one or more properties, such as antigen binding, stability, half-life, effector function, immunogenicity, safety and the like. Preferably the antibodies or antibody fragments according to the present disclosure are engineered or modified to improve effector function, such as ADCC.

The "Fc region" is used to define the C-terminal region of an immunoglobulin heavy chain. The Fc region of an immunoglobulin generally comprises two constant domains, a CH2 domain and a CH3 domain. Unless otherwise specified herein, numbering of amino acid residues in the Fc region is according to the EU numbering system, also called the EU index, as described in Kabat et al., Sequences of Proteins of Immunological Interest, $5^{th}$ Ed. Public Health Service, National Institutes of Health, Bethesda, MD, 1991.

The antibody which is administered according to the present disclosure is administered to the patient in a therapeutically effective amount. A "therapeutically effective amount" refers to an amount sufficient to provide some improvement of the clinical manifestations of a given disease or disorder. The amount that is effective for a particular therapeutic purpose will depend on the severity of the disease or injury as well as on the weight and general state of the subject. It will be understood that determination of an appropriate dosage may be achieved, using routine experimentation, by constructing a matrix of values and testing different points in the matrix, all of which is within the ordinary skills of a trained physician or clinical scientist.

The terms "combination" or "pharmaceutical combination" refer to the administration of one therapy in addition to another therapy. As such, "in combination with" includes simultaneous (e.g., concurrent) and consecutive administration in any order. By way of non-limiting example, a first therapy (e.g., agent, such as an anti-CD19 antibody) may be administered before (e.g., 1 minute, 15 minutes, 30 minutes, 45 minutes, 1 hour, 2 hours, 3 hours, 4 hours, 5 hours, 6 hours, 7 hours, 8 hours, 12 hours, 24 hours, 48 hours, 72 hours, 96 hours, 1 week, 2 weeks, 3 weeks, 4 weeks, 5 weeks, 6 weeks, 8 weeks, 8 weeks, 9 weeks, weeks, 11 weeks, or 12 weeks), concurrently, or after (e.g., 1 minute, 15 minutes, 30 minutes, 45 minutes, 1 hour, 2 hours, 3 hours, 4 hours, 5 hours, 6 hours, 7 hours, 8 hours, 12 hours, 24 hours, 48 hours, 72 hours, 96 hours, 1 week, 2 weeks, 3 weeks, 4 weeks, 5 weeks, 6 weeks, 7 weeks, 8 weeks, 9 weeks, 10 weeks, 11 weeks, or 12 weeks or longer) the administration of a second therapy (e.g., pharmaceutical agent, such as γδ T-cells) to a patient.

The term "γδ T-cells (gamma delta T-cells)" as used herein refers to a subset of T-cells that express a distinct T-cell receptor (TCR), γδTCR, on their surface, composed of one γ-chain and one δ-chain. The term "γδ T-cells" specifically includes all subsets of γδ T-cells, including, without limitation, vδ1, vδ2, vδ3 and Vγ9Vδ2 T-cells, as well as naive, effector memory, central memory, and terminally differentiated γδ T-cells. As a further example, the term "γδ T-cells" includes vδ4, vδ5, vδ7, and vδ8 T cells.

As used herein, the term "T lymphocyte" or "T-cell" refers to an immune cell expressing CD3 (CD3+) and a T Cell Receptor (TCR+). T cells play a central role in cell-mediated immunity.

As used herein, the term "TCR" or "T cell receptor" refers to a dimeric heterologous cell surface signaling protein forming an alpha-beta or gamma-delta receptor. αβTCR recognize an antigen presented by an MHC molecule, whereas γδTCR recognize an antigen independently of MHC presentation.

As used herein, the term "cell population" refers to a number of ceils. A cell population may be, for example, a mixed cell population derived from a peripheral blood sample, a coni blood sample, a tumor, a stem cell precursor, a tumor biopsy, a tissue, a lymph, or from epithelial sites of a subject directly contacting the external milieu, or derived from stem precursor cells. Alternatively, the mixed cell population may be derived from in vitro cultures of mammalian cells, established from a peripheral blood sample, a cord blood sample, a tumor, a stem cell precursor, a tumor biopsy, a tissue, a lymph, or from epithelial sites of a subject directly contacting the external milieu, or derived from stem precursor ceils.

An "enriched" cell population or preparation refers to a cell population derived from a starting mixed cell population that contains a greater percentage of a specific cell type than the percentage of that cell type in the starting population. For example, a starting mixed cell population can be enriched for a specific γδ T-cell population, in ail embodiments, the enriched γδ T-cell population contains a lesser percentage of αβ T-cell populations.

By "expanded" as used herein is meant that the number of the desired or target cell type (e.g., δ1, δ2 T-cells and/or Vγ9Vδ2 T-cells) in the enriched preparation is higher than the number in the initial or starting cell population.

DETAILED DESCRIPTION OF THE INVENTION

Anti-CD19 Antibodies

The use of a CD19 antibody in non-specific B cell lymphomas is discussed in WO2007076950 (US2007154473), which are both incorporated by reference. The use of a CD19 antibody in CLL, NHL and ALL is described in Scheuermann et al., CD19 Antigen in Leukemia and Lymphoma Diagnosis and Immunotherapy, Leukemia and Lymphoma, Vol. 18, 385-397 (1995), which is incorporated by reference in its entirety.

Additional antibodies specific for CD19 are described in WO2005012493 (U.S. Pat. No. 7,109,304), WO2010053716 (U.S. Ser. No. 12/266,999) (Immunomedics); WO2007002223 (US U.S. Pat. No. 8,097,703) (Medarex); WO2008022152 (Ser. No. 12/377,251) and WO2008150494 (Xencor), WO2008031056 (U.S. Ser. No. 11/852,106) (Medimmune); WO 2007076950 (U.S. Ser. No. 11/648,505) (Merck Patent GmbH); WO 2009/052431 (U.S. Ser. No. 12/253,895) (Seattle Genetics); and WO2010095031 (Ser. No. 12/710,442) (Glenmark Pharmaceuticals), WO2012010562 and WO2012010561 (International Drug Development), WO2011147834 (Roche Glycart), and WO2012156455 (Sanofi), which are all incorporated by reference in their entireties.

A pharmaceutical composition includes an active agent, e.g. an antibody for therapeutic use in humans. A pharmaceutical composition may additionally include pharmaceutically acceptable carriers or excipients.

The dose of an antibody or antibody fragment comprised in a pharmaceutical composition according to the present disclosure administered to a patient may vary depending upon the age and the size of the patient, symptoms, conditions, route of administration, and the like. The dose is typically calculated according to body weight, or body surface area, age, or per individual. Depending on the severity of the condition, the frequency and the duration of the treatment can be adjusted. Effective dosages and schedules for administering pharmaceutical compositions comprising antibodies or antibody fragments specific for CD19 may be determined empirically; for example, patient progress can be monitored by periodic assessment, and the dose adjusted accordingly. Moreover, interspecies scaling of dosages can be performed using well-known methods in the art (e.g., Mordenti et al., 1991, Pharmaceut. Res. 8:1351).

The pharmaceutical composition may include dosage forms for intravenous, subcutaneous, intracutaneous and intramuscular injections, etc. These injectable preparations may be prepared by known methods. For example, the injectable preparations may be prepared, e.g., by dissolving, suspending or emulsifying the antibody or its salt described above in a sterile aqueous medium or an oily medium conventionally used for injections. Exemplary pharmaceutical compositions comprising an antibody or antibody fragment specific for CD19 that can be used in the context of the present disclosure are disclosed, e.g., in WO2008/022152 or WO2018/002031.

In certain ways of administration, e.g. intravenous administration, it is preferred to administer drug depending on the body weight of the patient. In other ways of administration, e.g. subcutaneous administration, it is preferred to administer drug at a flat, fixed does. The skilled person is aware of which dose in one way of administration is equivalent to another dose in another way of administration. The pharmacodynamics of a specific drug are typically taken into account in a reasoned decision to administer a drug in the required from and at a required, efficacious dose.

The antibody which is administered according to the present disclosure is administered to the patient in a therapeutically effective amount. A "therapeutically effective amount" refers to an amount sufficient to cure, alleviate or partially arrest the clinical manifestations of a given disease or disorder, i.e. NHL, and its complications. In certain embodiments the antibodies of the present disclosure are administered at 9 mg/kg. In alternative embodiments the antibodies of the present disclosure are administered at 12 mg/kg. In yet other embodiments the antibodies of the present disclosure are administered at 15 mg/kg or more.

The antibody of the present disclosure can be administered at different time points and the treatment cycle may have a different length. The antibodies may be administered daily, every other day, three times a week, weekly or biweekly. The antibodies may also be administered over at least four weeks, over at least five weeks, over at least six weeks, over at least seven weeks, over at least eight weeks, over at least nine weeks, over at least ten weeks, over at least eleven weeks or over at least twelve weeks. In certain embodiments of the present disclosure the antibody is administered at least once weekly over at least eight weeks.

Isolation and Expansion of γδ T-Cells from Blood

In some embodiments, the γδ T-cells of the present disclosure are derived from blood (e.g., peripheral blood) of a subject. For example, γδ T-cells may be derived from blood-derived Vδ2 cells or blood-derived Vδ1 cells. In another example, γδ T-cells may be derived from blood-derived Vγ9Vδ2 T-cells. Vγ9Vδ2 T-cells can be isolated from peripheral blood and further cultivated ex vivo. Cultivation of Vγ9Vδ2 T-cells can be optimized in the presence of IL-2 and zoledronic acid (ZOL). Methods of isolating and expanding Vγ9Vδ2 T-cells from blood include those described, for example in Hoeres et al. 2018 or the following procedure:

Ex Vivo Expansion of Vγ9Vδ2 T Cells Derived from Peripheral Blood:

Peripheral blood is collected from donors. PBMC are isolated immediately via density gradient centrifugation using Lymphoprep™ (Axis Shield, Norway) following manufacturer's instructions. PBMCs to be resuspended to $1*10^6$/mL in CTS™ OpTmizer™ T Cell Expansion SFM (Life Technologies, Australia) supplemented with OpTmizer™ T cell Expansion Supplement (1:38 dilution) (Life Technologies, Australia), 10% heat-inactivated FBS (HI-FBS), 100 IU/mL penicillin, 100 μg/mL streptomycin, 2 mmol L-glutamine (Life Technologies, Australia), 25 mM HEPES, 0.1% β-mercaptoethanol (Sigma-Aldrich, USA), 100 IU/mL recombinant human interleukin 2 (rhIL-2) (BD Pharmingen, USA) and activated with 5 μM ZOL, and seeded into 6-well plates. Cell culture density to be maintained at $1\text{-}2*10^6$ cells/mL and replenished with fresh medium containing 100 IU/mL rhIL-2 only (without ZOL) every 2-3 days. Following 7-8 days of culture cells were collected and enriched as described below.

Enrichment of Vγ9Vδ2 T Cells:

Ex vivo expanded Vγ9Vδ2 T cells are enriched using negative selection MACS with the TCR γ/δ+ T cell Isolation Kit (human) (Miltenyi Biotec, Germany). Cell viability and total cells numbers after enrichment are assessed using trypan blue exclusion. Percentage of Vγ9Vδ2 T cells are determined by flow cytometry using PeCy5 conjugated anti-CD3 (clone UCHT1) (eBioscience, San Diego, CA, USA) and FiTC conjugated anti-Vγ9 TCR from BD Biosciences (San Jose, CA, USA). Percentages of Vγ9Vδ2 T cells are identified by gating on the lymphocyte population using forward scatter/side scatter then on Vγ9+CD3+ double positive cells.

In some embodiments, peripheral blood mononuclear cells (PBMCs) can be obtained from a subject according to any suitable method known in the art. PBMCs can be cultured in the presence of aminobisphosphonates (e.g., zoiedronic acid), synthetic phosphoantigens (e.g., bromohydrin pyrophosphate; BrHPP), 2M3B1PP, or 2-methyl-3-butenyl-1-pyrophosphate in the presence of IL-2 for one-to-two weeks to generate an enriched population of Vδ2 cells. Alternatively, immobilized anti-TCR γδ (e.g., pan TCR γδ) can induce preferential expansion of Vδ2 cells from a population of PBMCs in the presence of IL-2, e.g., for approximately 14 days. In some embodiments, preferential expansion of Vδ2 cells from PBMCs can be achieved upon culture of immobilized anti-CD3 antibodies (e.g., OKT3) in the presence of IL-2 and IL-4. In some embodiments, the aforementioned culture is maintained for about seven days prior to subculture in soluble anti-CD3, IL-2, and IL-4. Alternatively, artificial antigen presenting cells can be used to promote preferential expansion of γδ T cells, such as Vδ2 cells. For example, PBMC-derived γδ T-cells cultured in the presence of irradiated aAPC, IL-2, and/or IL-21 can expand to generate a population of γδ T cells including a high proportion of Vδ2 cells, moderate proportion of Vδ1 cells, and some double negative cells, in some embodiments of the aforementioned methods, PBMCs can be pre-enriched or post-enriched (e.g. through positive selection with TCRyd-specific agents or negative selection of TCRa-specific agents). Such methods and other suitable methods for expansion of γδ T cells, such as Vδ2 cells, are described in detail by Deniger et al., Frontiers in Immunology 2014, 5, 636: 1-10, which is incorporated herein by reference in its entirety. Moreover, Almeida et al. (Clinical Cancer Research 2016, 22, 23; 5795-5805), incorporated herein by reference in its entirety, provides suitable methods of obtaining a population of Vδ1 T-cells that can be engineered to express a heterologous targeting construct described herein. For example, in some embodiments, PBMCs are pre-enriched using magnetic bead sorting, which can yield greater than 90% γδ T cells.

Separation and Expansion of Non-Haematopoietic Tissue-Resident γδ T Cells from Non-Haematopoietic Tissue Non-haematopoietic tissue-resident γδ T cells obtained as described herein exhibit good tumor penetration and retention capabilities. More detailed methods for isolation and expansion of non-haematopoietic tissue-resident γδ T cells can be found, for example, in GB Application No. 1707048.3 (WO2018/202808) and in International Patent Publication No. WO 2017/072367 (US Publ. No. 2018/0312808), each of which is incorporated herein by reference in its entirety.

Non-haematopoietic tissue-resident γδ T cells (e.g., skin-derived γδ T ceils and/or non-Vδ2 T cells, e.g., Vδ1 T cells and/or DN T cells) can be isolated from any human or non-human animal non-haematopoietic tissue that can be removed from a patient to obtain cells suitable for engineering according to the methods of the present invention. In some embodiments, the non-haematopoietic tissue from which the γδ T cells are derived and expanded is skin (e.g., human skin), which can be obtained by methods known in the art. In some embodiments, the skin is obtained by punch biopsy. Alternatively, the methods of isolation and expansion of γδ T cells provided herein can be applied to the gastrointestinal tract (e.g., colon), mammary gland, lung, prostate, liver, spleen, and pancreas. The γδ T cells may also be resident in human cancer tissues, e.g., tumors of the breast or prostate. In some embodiments, the γδ T cells may be from human cancer tissues (e.g., solid tumor tissues). In other embodiments, the γδ T cells may be from non-haematopoietic tissue other than human cancer tissue (e.g., a tissue without a substantial number of tumor cells). For example, the γδ T cells may be from a region of skin (e.g., healthy skin) separate from a nearby or adjacent cancer tissue.

The γδ T cells that are dominant in the blood are primarily Vδ2 T cells, while the γδ T cells that are dominant in the non-haematopoietic tissues are primarily Vδ1 T cells, such that Vδ1 T cells include about 70-80% of the non-haematopoietic tissue-resident γδ T cell population. However, some Vδ2 T cells are also found in non-haematopoietic tissues, e.g. in the gut, where they can include about 10-20% of γδ T cells. Some γδ T cells that are resident in non-haematopoietic tissues express neither Vδ1 nor Vδ2 TCR and we have named them double negative (DN) γδ T ceils. These DN γδ T cells are likely to be mostly Vδ3-expressing with a minority of Vδ5-expressing T ceils. Therefore, the γδ T cells that are ordinarily resident in non-haematopoietic tissues and that are expanded by the method of the invention are preferably non-Vδ2 T cells, e.g. Vδ1 T cells, with the inclusion of a smaller amount of DN γδ T cells.

In general, non-haematopoietic tissue-resident γδ T ceils are capable of spontaneously expanding upon removal of physical contact with stromal cells (e.g., skin fibroblasts). Thus, the scaffold-based culture methods described above can be used to induce such separation, resulting in de repression of the γδ T ceils to trigger expansion. Accordingly, in some embodiments, no substantial TCR pathway activation is present during the expansion step (e.g., no exogenous TCR pathway activators are included in the culture). Further, the invention provides methods of expanding non-haematopoietic tissue-resident γδ T ceils, wherein the methods do not involve contact with feeder cells, tumor cells, and/or antigen-presenting cells.

Methods of Treatment

Pharmaceutical compositions containing a non-engineered, enriched γδ T-cell population, an engineered, enriched γδ T-cell population, and/or admixtures thereof, as described herein may be administered for prophylactic and/or therapeutic treatments, in therapeutic applications, the compositions can be administered to a subject already suffering from a disease or condition in an amount sufficient to cure or at least partially arrest the symptoms of the disease or condition. A non-engineered, enriched γδ T-cell population, an engineered, enriched γδ T-cell population, and/or admixtures thereof, can also be administered to lessen a likelihood of developing, contracting, or worsening a condition. Effective amounts of a population of a non-engineered, enriched γδ T-cell population, an engineered, enriched γδ T-cell population, and/or admixtures thereof, for therapeutic use can vary based on the severity and course of the disease or condition, previous therapy, the subject's health status, weight, and/or response to the drugs, and/or the judgment of the treating physician.

A non-engineered, enriched γδ T-cell population, an engineered, enriched γδ T-cell population, and/or admixtures thereof, of the disclosure can be used to treat a subject in need of treatment for a condition.

A method of treating a condition in a subject with an enriched γδ T-cell population and an antibody or antibody fragment specific for CD19 of the present disclosure may comprise administering to the subject a therapeutically-effective amount of a non-engineered, enriched γδ T-cell population, an engineered, enriched γδ T-cell population, and/or admixtures thereof. An enriched γδ T-cell population, and/or admixtures thereof, of the disclosure may be administered at various regimens (e.g., timing, concentration, dosage, spacing between treatment, and/or formulation). A subject can also be preconditioned with, for example, chemotherapy, radiation, or a combination of both, prior to receiving a an enriched γδ T-cell population and/or admixtures thereof, of the disclosure. As part of a treatment, a non-engineered, enriched γδ T-cell population, an engineered, enriched γδ T-cell population, and/or admixtures thereof, may be administered to a subject at a first regimen and the subject may be monitored to determine whether the treatment at the first regimen meets a given level of therapeutic efficacy.

An enriched γδ T-cell population, i.e., non-engineered or engineered, and/or admixtures thereof, of the disclosure may be used to treat various conditions. In some cases, a non-engineered, enriched γδ T-cell population, an engineered, enriched γδ T-cell population, and/or admixtures thereof, of the disclosure may be used to treat a cancer, including solid tumors and hematologic cancer.

Methods of Administration

One or multiple non-engineered, enriched γδ T-cell population, engineered, enriched γδ T-cell population, and/or admixtures thereof, of the invention can be administered to a subject in any order or simultaneously. If simultaneously, the multiple non-engineered, enriched γδ T-cell population, engineered, enriched γδ T-cell population, and/or admixtures thereof, of the invention can be provided in a single, unified form, such as an intravenous injection, or in multiple forms, for example, as multiple intravenous infusions, s.c, injections or pills. The non-engineered, enriched γδ T-cell population, engineered, enriched γδ T-cell population, and/or admixtures thereof, of the invention can be packed together or separately, in a single package or in a plurality of packages. One or all of the non-engineered, enriched γδ T-cell population, engineered, enriched γδ T-cell population, and/or admixtures thereof, of the invention can be given in multiple doses. If not simultaneous, the timing between the multiple doses may vary to as much as about a week, a month, two months, three months, four months, five months, six months, or about a year. In some cases, a non-engineered, enriched γδ T-cell population, an engineered, enriched γδ

T-cell population, and/or admixtures thereof, of the invention can expand within a subject's body, in vivo, after administration to a subject. Non-engineered, enriched γδ T-cell population, engineered, enriched γδ T-cell population, and/or admixtures thereof, can be frozen to provide cells for multiple treatments with the same cell preparation. Non-engineered, enriched γδ T-cell population, engineered, enriched γδ T-cell population, and/or admixtures thereof, of the disclosure, and pharmaceutical compositions comprising the same, can be packaged as a kit. A kit may include instructions (e.g., written instructions) on the use of the non-engineered, enriched γδ T-cell population, the engineered, enriched γδ T-cell population, and/or admixtures thereof, and compositions comprising the same.

In some cases, a method of treating a cancer comprises administering to a subject a therapeutically-effective amount of a non-engineered, enriched γδ T-cell population, an engineered, enriched γδ T-cell population, and/or admixtures thereof, wherein the administration treats the cancer. In some embodiments the therapeutically-effective amount of the non-engineered, enriched γδ T-cell population, the engineered, enriched γδ T-cell population, and/or admixtures thereof, is administered for at least about 10 seconds, 30 seconds, 1 minute, 10 minutes, 30 minutes, 1 hour, 2 hours, 3 hours, 4 hours, 5 hours, 5 hours, 12 hours, 24 hours, 2 days, 3 days, 4 days, 5 days, 6 days, 1 week, 2 weeks, 3 weeks, 1 month, 2 months, 3 months, 4 months, 5 months, 6 months, or 1 year, in some embodiments the therapeutically-effective amount of the non-engineered, enriched γδ T-cell population, the engineered, enriched γδ T-cell population, and/or admixtures thereof, is administered for at least one week. In some embodiments the therapeutically-effective amount of the non-engineered, enriched γδ T-cell population, the engineered, enriched γδ T-cell population, and/or admixtures thereof, is administered for at least two weeks.

EMBODIMENTS

The present disclosure provides a pharmaceutical combination, comprising an antibody or antibody fragment specific for CD19 and gamma delta T-cells (γδ T-cells) for use in the treatment of cancer.

In one aspect the present disclosure provides a pharmaceutical combination, comprising an antibody specific for CD19 and gamma delta T-ceils (γδ T-cell) for use in the treatment of cancer wherein the γδ T-ceils comprise an enriched γδ T-cell population. In one embodiment the enriched γδ T-cell population comprises non-engineered or engineered γδ T-cells and/or admixtures thereof. In a further embodiment the present disclosure provides a pharmaceutical combination, comprising an antibody specific for CD19 and an enriched γδ T-cell population for use in the treatment of cancer.

In another aspect the present disclosure provides a pharmaceutical combination, comprising an antibody specific for CD19 and gamma delta T-cells (γδ T-cell) for use in the treatment of cancer wherein the γδ T-cells comprise non-engineered or engineered γδ T-cells and/or admixtures thereof. In another embodiment the γδ T-cells are a population of non-engineered γδ T-cells. In yet another embodiment the γδ T-cells are a population of engineered γδ T-cells.

In one aspect the present disclosure provides a pharmaceutical combination, comprising an antibody specific for CD19 and gamma delta T-cells (γδ T-cell) for use in the treatment of cancer wherein the γδ T-cells are isolated from peripheral blood, tumor tissue or non-hematopoietic tissue. In one embodiment the γδ T-cells are isolated from peripheral blood. In another embodiment the γδ T-cells are a population of γδ T-cells isolated from peripheral blood.

In one aspect the present disclosure provides a pharmaceutical combination, comprising an antibody specific for CD19 and gamma delta T-cells (γδ T-cell) for use in the treatment of cancer wherein the cancer is a hematological cancer. In one embodiment the hematological cancer is chronic lymphocytic leukemia (CLL), non-Hodgkin's lymphoma (NHL), small lymphocytic lymphoma (SLL) or acute lymphoblastic leukemia (ALL). In another embodiment the hematological cancer is non-Hodgkin's lymphoma (NHL). In a further embodiment the non-Hodgkin's lymphoma is selected from the group consisting of follicular lymphoma, small lymphocytic lymphoma, mucosa-associated lymphoid tissue, marginal zone lymphoma, diffuse large B cell lymphoma, Burkitt's lymphoma and mantle cell lymphoma.

In certain embodiments the present disclosure provides a pharmaceutical combination, comprising an antibody or antibody fragment specific for CD19 and gamma delta T-cells (γδ T-cell) for use in the treatment of cancer wherein said antibody or antibody fragment specific for CD19 is administered at 9 mg/kg. In alternative embodiments the antibody or antibody fragment specific for CD19 is administered at 12 mg/kg. In yet other embodiments at 15 mg/kg or more.

In embodiments, the antibody or antibody fragment specific for CD19 has a cytotoxic activity. In embodiments, the antibody or antibody fragment specific for CD19 comprises a constant region having ADCC inducing activity. In embodiments, the antibody specific for CD19 induces ADCC.

In certain embodiments the present disclosure provides a pharmaceutical combination, comprising an antibody or antibody fragment specific for CD19 and gamma delta T-cells (γδ T-cells) for use in the treatment of cancer wherein the components of the combination, the antibody or antibody fragment specific for CD19 and the γδ T-cells are administered separately. In an embodiment, the γδ T-cells are administered prior to administration of the antibody or antibody fragment specific for CD19. In an embodiment, the antibody or antibody fragment specific for CD19 are administered prior to administration of the γδ T-cells. In embodiments, the components of the combination are administered at a time where both components (drugs) are active in the patient at the same time. It is implied by "synergism" that both drugs are active in the patient at the same time. In embodiments, the components of the combination are administered together, simultaneously, separately or subsequently, either physically or in time, in embodiments, the components of the combination are administered simultaneously.

In certain embodiments the present disclosure provides a pharmaceutical combination, comprising an antibody or antibody fragment specific for CD19 and γδ T-cells for use in the treatment of cancer wherein the anti-CD19 antibody is administered weekly, bi-weekly or monthly.

In certain embodiments the present disclosure provides a pharmaceutical combination, comprising an antibody or antibody fragment specific for CD19 and γδ T-cells for use in the treatment of cancer wherein said antibody or antibody fragment specific for CD19 is administered in a concentration of 12 mg/kg.

In certain embodiments the present disclosure provides a pharmaceutical combination, comprising an antibody or antibody fragment specific for CD19 and γδ T-cells for use in the treatment of cancer wherein said antibody or antibody fragment specific for CD19 is administered weekly, biweekly or monthly after a first administration on Day 1 and wherein the BCL-2 inhibitor is administered for the first time on Day 8. In a further embodiment the anti-CD19 antibody or antibody fragment thereof after a first administration on Day 1 is administered weekly for the first 3 months and bi-weekly for at least the next 3 months.

In one aspect the present disclosure provides an anti-CD19 antibody or antibody fragment thereof for use in the treatment of hematological cancer patients, wherein said hematologic cancer patient has non-Hodgkin's lymphoma and wherein said anti-CD19 antibody or antibody fragment thereof is administered in combination with γδ T-ceils.

In one aspect the present disclosure provides an anti-CD19 antibody or antibody fragment thereof for use in the treatment of hematological cancer patients, wherein said hematologic cancer patient has non-Hodgkin's lymphoma and wherein said anti-CD19 antibody or antibody fragment thereof is administered in combination with γδ T-cells. In one embodiment the hematological cancer patient has non-Hodgkin's lymphoma, wherein the non-Hodgkin's lymphoma is selected from the group consisting of follicular lymphoma, small lymphocytic lymphoma, mucosa-associated lymphoid tissue, marginal zone lymphoma, diffuse large B cell lymphoma, Burkitt's lymphoma and mantle cell lymphoma.

In an embodiment the anti-CD19 antibody or antibody fragment thereof for use in the treatment of hematological cancer patients in combination with γδ T-cells comprises an HCDR1 region comprising the sequence SYVMH (SEQ ID NO: 1), an HCDR2 region comprising the sequence NPYNDG (SEQ ID NO: 2), an HCDR3 region comprising the sequence GTYYYGTRVFDY (SEQ ID NO: 3), an LCDR1 region comprising the sequence RSSKSLQNVNGNTYLY (SEQ ID NO: 4), an LCDR2 region comprising the sequence RMSNLNS (SEQ ID NO: 5), and an LCDR3 region comprising the sequence MQHLEYPIT (SEQ ID NO: 6).

In a further embodiment the anti-CD19 antibody or antibody fragment thereof for use in the treatment of hematological cancer patients in combination with γδ T-cells comprises a variable heavy chain of the sequence

```
                                      (SEQ ID NO: 7)
EVQLVESGGGLVKPGGSLKLSCAASGYITTSYVMHWVRQAPGKGLEWI

GYINPYNDGTKYNEKFQGRVTISSDKSISTAYMELSSLRSEDTAMYYC

ARGTYYYGTRVFDYWGQGTLVTVSS
```

and a variable light chain of the sequence

```
                                      (SEQ ID NO: 8)
DIVMTQSPATLSLSPGERATLSCRSSKSLQNVNGNTYLYWFQQKPGQS

PQLLIYRMSNLNSGVPDRFSGSGSGTEFTLTISSLEPEDFAVYYCMQH

LEYPITFGAGTKLEIK.
```

In another embodiment of the present disclosure the anti-CD19 antibody or antibody fragment thereof is a human, humanized or chimeric antibody or antibody fragment. In another embodiment of the present disclosure the anti-CD19 antibody or antibody fragment thereof is of the IgG isotype. In another embodiment the antibody or antibody fragment is IgG1, IgG2 or IgG1/IgG2 chimeric. In another embodiment of the present disclosure the isotype of the anti-CD19 antibody is engineered to enhance antibody-dependent cell-mediated cytotoxicity. In another embodiment the heavy chain constant region of the anti-CD19 antibody comprises amino acids 239D and 332E, wherein the Fc numbering is according to the EU index as in Kabat. In another embodiment the antibody is IgG1, IgG2 or IgG1/IgG2 and the chimeric heavy chain constant region of the anti-CD19 antibody comprises amino acids 239D and 332E, wherein the Fc numbering is according to the EU index as in Kabat.

In a further embodiment the anti-CD19 antibody for use in the treatment of hematological cancer patients in combination with γδ T-cells comprises a heavy chain having the sequence

```
                                       (SEQ ID NO: 11)
EVQLVESGGGLVKPGGSLKLSCAASGYTFTSYVMHWVRQAPGKGLEWIGY

INPYNDGTKYNEKFQGRVTISSDKSISTAYMELSSLRSEDTAMYYCARGT

YYYGTRVFDYWGQGTLVTVSSASTKGPSVFPLAPSSKSTSGGTAALGCLV

KDYFPEPVTVSWNSGALTSGVHTFPAVLQSSGLYSLSSVVTVPSSSLGTQ

TYICNVNHKPSNTKVDKKVEPKSCDKTHTCPPCPAPELLGGPDVFLFPPK

PKDTLMISRTPEVTCVVVDVSHEDPEVQFNWYVDGVEVHNAKTKPREEQF

NSTFRVVSVLTVVHQDWLNGKEYKCKVSNKALPAPEEKTISKTKGQPREP

QVYTLPPSREEMTKNQVSLICLVKGFYPSDIAVEWESNGQPENNYKTTPP

MLDSDGSFFLYSKLTVDKSRWQQGNVFSCSVMHEALHNHYTQKSLSLSPG

K
```

and a light chain having the sequence

```
                                       (SEQ ID NO: 12)
DIVMTQSPATLKSPGERATLSCRSSKSLQNVNGNTYLYWFQQKPGQSPQL

LIYRMSNLNSGVPDRFSGSGSGTEFTLTISSLEPEDFAVYYCMQHLEYPI

TFGAGTKLEIKRTVAAPSVFIFPPFSDEQLKSGTASVVCLLNNFYPREAKV

QWKVDNALQSGNSQESVTEQDSKDSTYSLSSTLTLSKADYEKHKVYACEV

THQGLSSPVTKSFNRGEC.
```

In an embodiment the anti-CD19 antibody or antibody fragment thereof for use in the treatment of hematological cancer patients in combination with γδ T-cells comprises a variable heavy chain of the sequence

```
                                        (SEQ ID NO: 7)
EVQLVESGGGLVKPGGSLKLSCAASGYTFTSYVMHWVRQAPGKGLEWIGY

INPYNDGTKYNEKFQGRVTISSDKSISTAYMELSSLRSEDTAMYYCARGT

YYYGTRVFDYWGQGTLVTVSS
```

and a variable light chain of the sequence

```
                                        (SEQ ID NO: 8)
DIVMTQSPATLSLSPGERATLSCRSSKSLQNVNGNTYLYINFQQKPGQSP

QLLIYRMSNLNSGVPDRFSGSGSGTEFTLTISSLEPEDFAVYYCMQHLEY

PITFGAGTKLEIK
```

or a variable heavy chain and a variable light chain that has at least 80%, at least 90%, at least 95%, at least 96%, at least 97%, at least 98% or at least 99% identity to the variable heavy chain of SEQ ID NO: 7 and to the variable light chain of SEQ ID NO: 8.

In an embodiment the anti-CD19 antibody or antibody fragment thereof for use in the treatment of hematological cancer patients in combination with γδ T-cells comprises a variable heavy chain of the sequence (SEQ ID NO: 7)
EVQLVESGGGLVKPGGSLKLSCAASGYTFTSYVMHWVRQAPGKGLEWIGY

INPYNDGTKYNEKFQGRVTISSDKSISTAYMELSSLRSEDTAMYYCARGT

YYYGTRVFDYWGQGTLVTVSS and a variable light chain of the sequence (SEQ ID NO: 8)
DIVMTQSPATLSLSPGERATLSCRSSKSLQNVNGNTYLYWFQQKPGQSPQ

LLIYRMSNLNSGVPDRFSGSGSGTEFTLTISSLEPEDFAVYYCMQHLEYP

ITFGAGTKLEIK or a variable heavy chain and a variable light chain that has at least 80%, at least 90%, at least 95%, at least 96%, at least 97%, at least 98% or at least 99% identity to the variable heavy chain of SEQ ID NO: 7 and to the variable light chain of SEQ ID NO: 8, wherein the anti-CD19 antibody comprises an HCDR1 region comprising the sequence SYVMH (SEQ ID NO: 1), an HCDR2 region comprising the sequence NPYNDG (SEQ ID NO: 2), an HCDR3 region comprising the sequence GTYYYGTRVFDY (SEQ ID NO: 3), an LCDR1 region comprising the sequence RSSKSLQNVNGNTYLY (SEQ ID NO: 4), an LCDR2 region comprising the sequence RMSNLNS (SEQ ID NO: 5), and an LCDR3 region comprising the sequence MQHLEYPIT (SEQ ID NO: 6). In another embodiment the heavy chain region of the anti-CD19 antibody comprises amino acids 239D and 332E, wherein the Fc numbering is according to the EU index as in Kabat.

In a further embodiment the anti-CD19 antibody or antibody fragment thereof for use in the treatment of hematological cancer patients in combination with γδ T-cells comprises a heavy chain having the sequence (SEQ ID NO: 11)
EVQLVESGGGLVKPGGSLKLSCAASGYTFTSYVMHWVRQAPGKGLEWIGY

INPYNDGTKYNEKFQGRVTISSDKSISTAYMELSSLRSEDTAMYYCARGT

YYYGTRVFDYWGQGTLVTVSSASTKGPSVFPLAPSSKSTSGGTAALGCLV

KDYFPEPVTVSWNSGALTSGVHTFPAVLQSSGLYSLSSVVTVPSSSLGTQ

TYICNVNHKPSNTKVDKKVEPKSCDKTHTCPPCPAPELLGGPDVFLFPFK

PKDILMISRTPEVICVVVDVSHEDPEVQFNWYVDGVEVHNAKTKPREEQF

NSTFRVVSVLTVVHQDWLNGKEYKCKVSNKALPAFEEKTISKTKGQPREP

QVYTLPPSREEMTKNQVSLTCLVKGFYPSDIAVEWESNGQPENNYKTTPF

MLDSDGSFFLYSKLTVDKSRWQQGNVFSCSVMHEALHNHYTQKSLSLSPG

K and a light chain having the sequence (SEQ ID NO: 12)
DIVMTQSPATLSLSPGERATLSCRSSKSLQNVNGNTYLYWFQQKPGQSPQ

LLIYRMSNLNSGVPDRFSGSGSGTEFTLTISSLEPEDFAVYYCMQHLEYP

-continued

ITFGAGTKLEIKRTVAAPSVFIFPPSDEQLKSGTASVVCLLNNFYFREAK

VQWKVDNALQSGNSQESVTEQDSKDSTYSLSSTLTLSKADYEKHKVYACE

VTHQGLSSPVTKSFNRGEC or a heavy chain and a light chain that has at least 80%, at least 90%, at least 95%, at least 96%, at least 97%, at least 98% or at least 99% identity to the heavy chain of SEQ ID NO: 7 and to the light chain of SEQ ID NO: 8.

In a further embodiment the anti-CD19 antibody or antibody fragment thereof for use in the treatment of hematological cancer patients in combination with γδ T-cells comprises a heavy chain having the sequence (SEQ ID NO: 11)
EVQLVESGGGLVKPGGSLKLSCAASGYTFTSYVMHWVRQAPGKGLEWIGY

INPYNDGTKYNEKFQGRVTISSDKSISTAYMELSSLRSEDTAMYYCARGT

YYYGTRVFDYWGQGTLVTVSSASTKGPSVFPLAPSSKSTSGGTAALGCLV

KDYFPEPVWSWNSGALTSGVHTFPAVLQSSGLYSLSSVVTVPSSSLGTQT

YICNVNHKPSNTKVDKKVEPKSCDKTFITCPPCPAPELLGGPDVFLFPPK

PKDTLMISRTPEVICVVVDVSHEDPEVQFNWYVDGVEVHNAKTKPREEQF

NSTFRVVSVLTVVFIQDWLNGKEYKCKVSNKALPAPEEKTISKTKGQPRE

PQVYTLPPSREEMTKNQVSLICLVKGFYPSDIAVEWESNGQPENNYKTTP

PMLDSDGSFFLYSKLTVDKSRWQQGNVFSCSVMHEALHNHYTQKSLSLSP

GK and a tight chain having the sequence (SEQ ID NO: 12)
DIVMTQSPAITSLSPGERATLSCRSSKSLQNVNGNTYLYWFQQKPGQSPQ

LLIYRMSNLNSGVPDRFSGSGSGTEFTLTISSLEPEDFAVYYCMQHLEYP

ITFGAGTKLEIKRTVAAPSVF1FPPSDEQLKSGTASVVCLLNNFYPREAK

VQWKVDNALQSGNSQESVTEQDSKDSTYSLSSTLTLSKADYEKHKVYACE

VITIQGLSSPVIKSFNRGEC or a heavy chain and a light chain that has at least 80%, at least 90%, at least 95%, at least 96%, at least 97%, at least 98% or at least 99% identity to the heavy chain of SEQ ID NO: 7 and to the light chain of SEQ ID NO: 8 and wherein the anti-CD19 antibody comprises an HCDR1 region comprising the sequence SYVMH (SEQ ID NO: 1), an HCDR2 region comprising the sequence NPYNDG (SEQ ID NO: 2), an HCDR3 region comprising the sequence GTYYYGTRVFDY (SEQ ID NO: 3), an LCDR1 region comprising the sequence RSSKSLQNVNGNTYLY (SEQ ID NO: 4), an LCDR2 region comprising the sequence RMSNLNS (SEQ ID NO: 5), and an LCDR3 region comprising the sequence MQHLEYPIT (SEQ ID NO: 6). In another embodiment the heavy chain region of the anti-CD19 antibody comprises amino acids 239D and 332E, wherein the Fc numbering is according to the EU index as in Kabat.

In one embodiment the present disclosure provides an anti-CD19 antibody or antibody fragment thereof wherein said anti-CD19 antibody or antibody fragment thereof is administered in a concentration of 12 mg/kg.

In a further embodiment, the anti-CD19 antibody or antibody fragment thereof is administered weekly, bi-weekly or monthly. In a further embodiment the anti-CD19 antibody or antibody fragment thereof is administered weekly for the first 3 months and bi-weekly for at least the next 3 months. In a further embodiment, the anti-CD19 antibody or antibody fragment thereof is administered weekly for the first 3 months. In a further embodiment the anti-CD19 antibody or antibody fragment thereof is administered weekly for the first 3 months and bi-weekly for at least the next 3 months. In another embodiment the anti-CD19 antibody or antibody fragment thereof is administered weekly for the first 3 months, bi-weekly for the next 3 months and monthly thereafter. In yet another embodiment the anti-CD19 antibody or antibody fragment thereof is administered weekly for the first 3 months, bi-weekly for the next 3 months and monthly thereafter.

The present disclosure provides an antibody or antibody fragment specific for CD19 for use in the treatment of cancer wherein said antibody or antibody fragment specific for CD19 is administered in combination with γδ T-cells. In one embodiment the γδ T-cells are isolated from peripheral blood, tumor tissue or non-hematopoietic tissue. In one embodiment the γδ T-cells are isolated from peripheral blood. In another embodiment the γδ T-cells are a population of γδ T-cells isolated from peripheral blood. In another embodiment the γδ T-cells are a population of γδ T-cells isolated from peripheral blood and cultivated in the presence of IL-2 and ZOL. In another example, the γδ T-cells are a population of blood-derived Vγ9Vδ2 T-cells.

The present disclosure provides an antibody or antibody fragment specific for CD19 for use in the treatment of cancer wherein said antibody or antibody fragment specific for CD19 is administered in combination with γδ T-cells wherein the step of administering is carried out by administering the antibody specific for CD19 and the γδ T-cells in combination in a simultaneous, in order, or in reverse-order manner.

In another embodiment the present disclosure provides the use of a pharmaceutical combination comprising an antibody or antibody fragment specific for CD19 and γδ T-cells for preparing a medicament for treatment of cancer.

In another embodiment the present disclosure provides a method for use in the treatment of cancer, comprising a step of administering, to a subject, an antibody specific for CD19 and an γδ T-cells in combination. In another embodiment the present disclosure provides a method for use in the treatment of cancer, comprising a step of administering, to a subject, an antibody specific for CD19 and an γδ T-cells in combination wherein the step of administering is carried out by administering the antibody specific for CD19 and the γδ T-cells in combination in a simultaneous, in order, or in reverse-order manner.

The present disclosure provides a pharmaceutical combination, comprising an antibody or antibody fragment specific for CD19 and gamma delta T-cells (γδ T-cell) for use in the treatment of cancer wherein the γδ T-cells are administered in a therapeutically effective amount. In some embodiments, a therapeutically effective amount of lymphocytes (e.g., γδ T cells) obtained by any of the methods described above can be administered in a therapeutically effective amount to a subject (e.g., for treatment of cancer such as hematologic cancer). In some cases, the therapeutically effective amount of lymphocytes (e.g., γδ T cells) is less than $10\times10^{12}$ cells per dose (e.g., less than $9\times10^{12}$ cells per dose, less than $8\times10^{12}$ cells per dose, less than $7\times10^{12}$ cells per dose, less than $6\times10^{12}$ ceils per dose, less than $5\times10^{12}$ cells per dose, less than $4\times10^{12}$ ceils per dose, less than $3\times10^{12}$ cells per dose, less than $2\times10^{12}$ cells per dose, less than $1\times10^{12}$ cells per dose, less than $9\times10^{11}$ cells per dose, less than $8\times10^{11}$ cells per dose, less than $7\times10^{11}$ cells per dose, less than $6\times10^{11}$ cells per dose, less than $5\times10^{11}$ cells per dose, less than $4\times10^{11}$ cells per dose, less than $3\times10^{11}$ cells per dose, less than $2\times10^{11}$ cells per dose, less than $1\times10^{11}$ cells per dose, less than $9\times10^{10}$ cells per dose, less than $7.5\times10^{10}$ cells per dose, less than $5\times10^{10}$ cells per dose, less than $2.5\times10^{10}$ cells per dose, less than $1\times10^{10}$ cells per dose, less than $7.5\times10^{9}$ cells per dose, less than $5\times10^{9}$ cells per dose, less than $2.5\times10^{9}$ cells per dose, less than $1\times10^{9}$ cells per dose, less than $7.5\times10^{e}$ cells per dose, less than $5\times10^{8}$ cells per dose, less than $2.5\times10^{5}$ cells per dose, less than $1\times10^{8}$ cells per dose, less than $7.5\times10^{7}$ cells per dose, less than $5\times10^{7}$ cells per dose, less than $2.5\times10^{7}$ cells per dose, less than $1\times10^{7}$ cells per dose, less than $7.5\times10^{6}$ cells per dose, less than $5\times10^{6}$ cells per dose, less than $2.5\times10^{6}$ cells per dose, less than $1\times10^{8}$ cells per dose, less than $7.5\times10^{5}$ ceils per dose, less than $5\times10^{5}$ cells per dose, less than $2.5\times10^{5}$ cells per dose, or less than $1\times10^{5}$ cells per dose).

In some embodiments, the therapeutically effective amount of γδ T-cells (e.g. skin-derived γδ T cells, blood-derived γδ T ceils) is less than $10\times10^{12}$ cells over the course of treatment (e.g., less than $9\times10^{12}$ ceils, less than $8\times10^{12}$ cells, less than $7\times10^{12}$ ceils, less than $6\times10^{12}$ cells, less than $5\times10^{1Z}$ cells, less than $4\times10^{12}$ cells, less than $3\times10^{12}$ cells, less than $2\times10^{12}$ ceils, less than $1\times10^{12}$ cells, less than $9\times10^{11}$ cells, less than $8\times10^{11}$ cells, less than $7\times10^{11}$ cells, less than $6\times10^{11}$ cells, less than $5\times10^{11}$ cells, less than $4\times10^{11}$ ceils, less than $3\times10^{11}$ cells, less than $2\times10^{11}$ cells, less than $1\times10^{11}$ ceils, less than $9\times10^{10}$ ceils, less than $7.5\times10^{10}$ cells, less than $5\times10^{10}$ cells, less than $2.5\times10^{10}$ cells, less than $1\times10^{10}$ cells, less than $7.5\times10^{9}$ cells, less than $5\times10^{B}$ cells, less than $2.5\times10^{9}$ cells, less than $1\times10^{9}$ cells, less than $7.5\times10^{5}$ cells, less than $5\times10^{8}$ cells, less than $2.5\times10^{8}$ cells, less than $1\times10^{8}$ cells, less than $7.5\times10^{7}$ cells, less than $5\times10^{7}$ ceils, less than $2.5\times10^{7}$ cells, less than $1\times10^{7}$ cells, less than $7.5\times10^{6}$ cells, less than $5\times10^{6}$ cells, less than $2.5\times10^{6}$ cells, less than $1\times10^{6}$ cells, less than $7.5\times10^{5}$ cells, less than $5\times10^{5}$ cells, less than $2.5\times10^{5}$ cells, or less than $1\times10^{5}$ cells over the course of treatment).

In some embodiments, a dose of γδ T-cells as described herein includes about $1\times10^{6}$, $1.1\times10^{6}$, $2\times10^{6}$, $3.6\times10^{6}$, $5\times10^{6}$, $1\times10^{7}$, $1.8\times10^{7}$, $2\times10^{7}$, $5\times10^{7}$, $1\times10^{8}$, $2\times10^{8}$, or $5\times10^{8}$ cells/kg. In some embodiments, a dose of γδ T-cells as described herein includes at least $1\times10^{6}$, $1.1\times10^{6}$, $2\times10^{6}$, $3.6\times10^{6}$, $5\times10^{5}$, $1\times10^{7}$, $1.8\times10^{7}$, $2\times10^{7}$, $5\times10^{7}$, $1\times10^{8}$, $2\times10^{5}$, or $5\times10^{8}$ cells/kg. In some embodiments, a dose of γδ T-cells as described herein includes up to $1\times10^{6}$, $1.1\times10^{6}$, $2\times10^{6}$, $3.6\times10^{6}$, $5\times10^{6}$, $1\times10^{7}$, $1.8\times10^{7}$, $2\times10^{7}$, $5\times10^{7}$, $1\times10^{8}$, $2\times10^{8}$, or $5\times10^{8}$ cells/kg.

Combinations

The present disclosure provides an anti-CD19 antibody or antibody fragment thereof in combination with γδ T-cells for use in the treatment of hematological cancer wherein said anti-CD19 antibody or antibody fragment thereof and γδ T-ceils are administered in combination with one or more pharmaceutical agents. In one embodiment of the present disclosure said anti-CD19 antibody or antibody fragment thereof and γδ T-cells are administered in combination with a pharmaceutical agent. In another embodiment of the present disclosure said anti-CD19 antibody or antibody fragment thereof and γδ T-cells are administered in combination with one or more additional pharmaceutical agents or an additional pharmaceutical agent. In one aspect said pharmaceutical agent is an additional pharmaceutical agent.

In one embodiment of the present disclosure said pharmaceutical agent is a biologic or a chemotherapeutic agent. In another embodiment of the present disclosure said pharmaceutical agent is a therapeutic antibody or antibody fragment, a nitrogen mustard, a purine analog, a thalidomide analog, a phosphoinositide 3-kinase inhibitor, a BCL-2 inhibitor or a bruton's tyrosine kinase (BTK) inhibitor. In a further embodiment said pharmaceutical agent is rituximab, R-CHOP, cyclophosphamide, chlorambucil, uramustine, ifosfamide, melphalan, bendamustine, mercaptopurine, azathioprine, thioguanine, fludarabine, thalidomide, lenalidomide, pomalidomide, idelalisib, duvelisib, copanlisib, ibrutinib or venetoclax.

In another embodiment the present disclosure provides an anti-CD19 antibody or antibody fragment thereof and γδ T-cells for use in the treatment of hematological cancer wherein said anti-CD19 antibody or antibody fragment thereof and γδ T-cells are administered in combination with rituximab, R-CHOP, cyclophosphamide, chlorambucil, uramustine, ifosfamide, melphalan, bendamustine, mercaptopurine, azathioprine, thioguanine, fludarabine, thalidomide, lenalidomide, pomalidomide, idelalisib, duvelisib, copanlisib, ibrutinib or venetoclax.

Antibody Sequences

TABLE 1

| | SEQ ID NO: | Amino Acids |
|---|---|---|
| HCDR1 | SEQ ID NO: 1 | SYVMH |
| HCDR2 | SEQ ID NO: 2 | NPYNDG |
| HCDR3 | SEQ ID NO: 3 | GTYYYGTRVFDY |
| LCDR1 | SEQ ID NO: 4 | RSSKSLQNVNGNTYLY |
| LCDR2 | SEQ ID NO: 5 | RMSNLNS |
| LCDR3 | SEQ ID NO: 6 | MQHLEYPIT |
| VH | SEQ ID NO: 7 | EVQLVESGGGLVKPGGSLKLSCAASGYTFTSY<br>VMHWVRQAPGKGLEWIGYINPYNDGTKYNEK<br>FQGRVTISSDKSISTAYMELSSLRSEDTAMYYC<br>ARGTYYYGTRVFDYWGQGTLVTVSS |
| VL | SEQ ID NO: 8 | DIVMTQSPATLSLSPGERATLSCRSSKSLQNV<br>NGNTYLYWFQQKPGQSPQLLIYRMSNLNSGV<br>PDRFSGSGSGTEFTLTISSLEPEDFAVYYCMQ<br>HLEYPITFGAGTKLEIK |
| Heavy chain constant domain | SEQ ID NO: 9 | ASTKGPSVFPLAPSSKSTSGGTAALGCLVKDY<br>FPEPVTVSWNSGALTSGVHTFPAVLQSSGLYS<br>LSSVVIVPSSSLGTQTYICNVNHKPSNTKVDK<br>KVEPKSCDKTHTCPPCPAPELLGGPDVFLFPP<br>KPKDTLMISRTPEVTCVVVDVSHEDPEVQFNW<br>YVDGVEVHNAKTKPREEQFNSTERVVSVLTVV<br>HQDWLNGKEYKCKVSNKALPAPEEKTISKTKG<br>QPREPQVYTLPPSREEMTKNQVSLTCLVKGFY<br>PSDIAVEWESNGQPENNYKTTPPMLDSDGSF<br>FLYSKLTVDKSRWQQGNVFSCSVMHEALHNH<br>YTQKSLSLSPGK |
| Light chain constant domain | SEQ ID NO: 10 | RTVAAPSVFIFPPSDEQLKSGTASVVCLLNNFY<br>PREAKVQWKVDNALQSGNSQESVTEQDSKD<br>STYSLSSTLTLSKADYEKHKVYACEVTHQGLS<br>SPVTKSFNRGEC |
| Full Heavy chain | SEQ ID NO: 11 | EVQLVESGGGLVKPGGSLKLSCAASGYTFTSY<br>VMHWVRQAPGKGLEWIGYINPYNDGTKYNEK<br>FQGRVTISSDKSISTAYMELSSLRSEDTAMYYC<br>ARGTYYYGTRVFDYWGQGTLVTVSSASTKGP<br>SVFPLAPSSKSTSGGTAALGCLVKDYFPEPVT<br>VSWNSGALTSGVHTFPAVLQSSGLYSLSSVVT<br>VPSSSLGTQTYICNVNHKPSNTKVDKKVEPKS<br>CDKTHTCPPCPAPELLGGPDVFLFPPKPKDTL<br>MISRTPEVTCVVVDVSHEDPEVQFNWYVDGV<br>EVHNAKTKPREEQFNSTFRVVSVLTVVHQDW<br>LNGKEYKCKVSNKALPAPEEKTISKTKGQPRE<br>PQVYTLPPSREEMTKNQVSLTCLVKGFYPSDI<br>AVEWESNGQPENNYKTTPPMLDSDGSFFLYS<br>KLTVDKSRWQQGNVFSCSVMHEALHNHYTQK<br>SLSLSPGK |

TABLE 1-continued

| | SEQ ID NO: | Amino Acids |
|---|---|---|
| Full Light chain | SEQ ID NO: 12 | DIVMTQSPATLSLSPGERATLSCRSSKSLQNV NGNTYLYWFQQKPGQSPQLLIYRMSNLNSGV PDRFSGSGSGTEFTLTISSLEPEDFAVYYCMQ HLEYPITFGAGTKLEIKRTVAAPSVFIFPPSDEQ LKSGTASVVCLLNNFYPREAKVQWKVDNALQ SGNSQESVTEQDSKDSTYSLSSTLTLSKADYE KHKVYACEVTHQGLSSPVTKSFNRGEC |

Examples

Example 1: Characterization of CD19 and CD20 Expression on Tested Cell Lines This study was performed to evaluate the cytotoxic activity of the Fc-enhanced anti-CD19 antibody tafasitamab (MOR00208) mediated by γδ T-cells from different donors on lymphoma and leukemia cell lines as well as primary patient-derived tumor material from CLL (Chronic Lymphocytic Leukemia), MCL (Mantle Cell Lymphoma) and B-ALL (Acute Lymphoblastic Leukemia). Furthermore, the antibody dependent cell-mediated cytotoxic activity of Tafasitamab in the presence of γδ T-cells was evaluated.

Different lymphoma and leukemia cell lines as well as patient-derived primary tumor cells from lymphoma and leukemia patients were evaluated in an antibody dependent cell-mediated cytotoxicity (ADCC) assay with various concentrations of tafasitamab and an IgG1 negative control antibody. The γδ T-cells were isolated from seven different donors and were used as effector cells at different effector to target cell ratios (E:T ratios 0.7:1, 2.2:1, 6.7:1 and 20:1).

Material, Methods & Data Analysis

γδ T-Cells:

γδ T-cells express Vγ and Vδ variable chains as part of a T-cell receptor (TCR) complex that is structurally and functionally distinctive from the major histocompatibility complex (MFIC) binding TCR of αβ T-cells. Despite unrestricted and high combinatorial diversity, the Vδ2 chain is preferentially paired with the Vγ9 chain. The Vγ9Vδ2 T-cells account for approximately 5% of peripheral blood T-cells, representing the dominant γδ T-cell subpopulation in this compartment. γδ T-cells from 7 different donors were isolated, stimulated and applied as listed in the following:

| Donor | Characteristics | Assay |
|---|---|---|
| 1 | d10 after stimulation with Zoledronate/IL2, TCRγδpos/CD3+: 36.5%, TCRγδneg/CD3+: 57.0%, CD56+/CD3−: 0.5% | Dose titration with Jeko cells |
| 2 | d10 after stimulation with Zoledronaet/IL2: TCRγδpos/CD3+: 84.8%, TCRγδneg/CD3+: 11.7%, CD56+/CD3−: 1.2% | Dose titration with U2932 cells |
| 3 | d9 after stimulation with Zoledronate/IL2, TCRγδpos/CD3+: 46.0%, TCRγδneg/CD3+: 47.0%, CD56+/CD3−: 1.75% | Dose titration with Jeko cells |
| 4 | d9 after stimulation with Zoledronate/IL2, TCRγδpos/CD3+: 60.8%, TCRγδneg/CD3+: 12.6%, CD56+/CD3−: 1.4% | Cytotoxicity cell lines |
| 5 | d9 after stimulation with Zoledronate/IL2, TCRγδpos/CD3+: 69.5%, TCRγδneg/CD3+: 23.2%, CD56+/CD3−: 2.6% | Cytotoxicity cell lines |

-continued

| Donor | Characteristics | Assay |
|---|---|---|
| 6 | d9 after stimulation with Zoledronate/IL2, TCRγδpos/CD3+: 84.8%, TCRγδneg/CD3+: 11.7%, CD56+/CD3−: 1.2% | Cytotoxicity cell lines |
| 7 | d9 after stimulation with Zoledronate/IL2, TCRγδpos/CD3+: 67.3%, TCRγδneg/CD3+: 24.4%, CD56+/CD3−: 3.6% | Cytotoxicity patient cells |

As listed in the table, the stimulated cell population used for the described experiments consisted of three main populations. Only a very small portion of CD56+/CD3− NK effector cells was present (<5%), while TCRγδneg/CD3+ cells represented a bigger population in some cases, but these cells do not trigger lysis of target cells. Therefore, mainly the γδ T-cells were responsible for antibody-mediated cell killing.

Cell Lines and Patient Samples

- Cell lines (obtained from DSMZ): Mino (Mantle cell lymphoma), Daudi (Burkitt's lymphoma), Jeko-1 (Mantle cell lymphoma), U2932 (DLBCL), REH (B-ALL)
- Patient samples (peripheral blood): 2×CLL (Chronic Lymphocytic Leukemia), 2×MCL (Mantle Cell Lymphoma), 1×B-ALL (Acute Lymphoblastic Leukemia)

Results

Dose Titration with Lymphoma Cell Lines

Initial dose titration experiments for getting a valid assay set-up were performed with MOR00208 at concentrations between 0.001 and 10 μg/mi in presence of four E:T ratios of T-cells (0.7:1, 2.2:1, 6.7:1 and 20:1) and a dose-dependent increase in the percentage of lysed Jeko and U2932 target cells was observed. As expected the killing activity of the tested antibodies increased with higher E:T ratios and most distinct effects were observed at the highest tested E:T ratios of 6.7:1 and 20:1. Maximum efficacy of cell lysis was reached at concentrations of 0.1 μg/ml, 1 μg/ml and 10 μg/ml MOR00208 in the two tested cell lines. Cell lysis showed γδ T-cell dependent donor variations with maximal lysis between 34.0% and 49.3% for Jeko and 22.5% for U2392 ceils, respectively. A concentration of 1 μg/ml of MOR00208 (Fc-enhanced) was selected as the optimal concentration for further comprehensive analyses of the Fc-dependent effect of antibody-mediated cell killing by γδ T-cells towards leukemia and lymphoma cell lines and patient derived tumor cells.

Cytotoxicity Assays with Lymphoma/Leukemia Cell Lines

Figure 2:
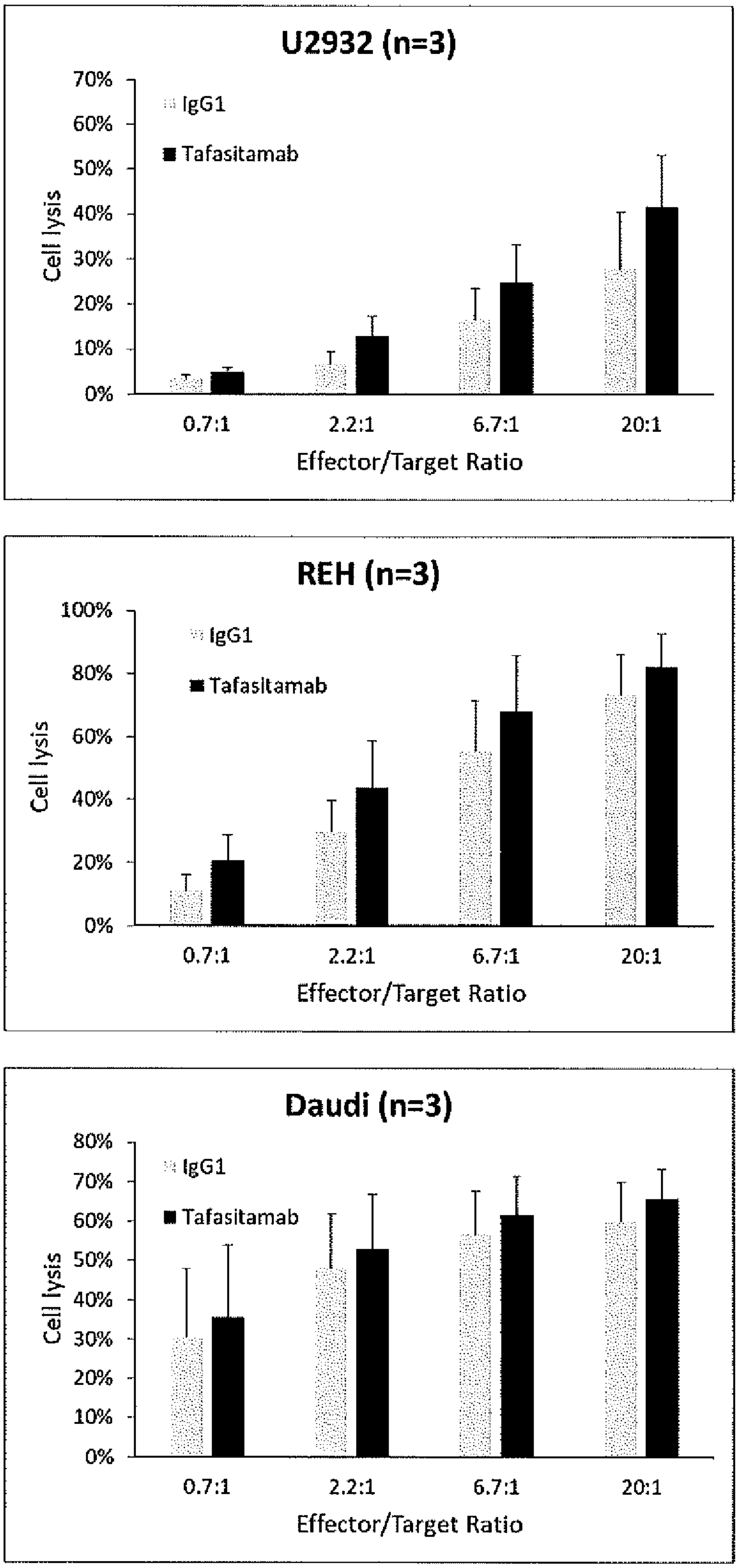
FIG. 2: Representative ADCC assays of MOR00208 at increasing effector to target cell (E:T) ratios. Results for specific cell killing expressed as % dead target cells mediated by MOR00208 (black) or the IgG1 control (white) and γδ T-cells from healthy donors are depicted for three target cell lines U2932 and REH. Four different E:T ratios between 0.7:1 and 20:1 were tested.

To determine the tumor cell killing potential of γδ T-cells in combination with CD19 antibodies, Tafasitamab was tested at 1 μg/ml with Mino, Daudi, Jeko, U2932 and REH cells as target cells (FIG. 1 and FIG. 2). As before four different E:T ratios between 0.7:1 and 20:1 were tested. And for all cell lines the effects of MOR00208 in combination with γδ T-cells were superior to the IgG1 control (MOR00208>IgG1 control) in combination with γδ T-cells. As observed during the dose titration experiments killing activity of the tested antibody increased and most distinct effects were found at the highest tested E:T ratios of 6.7:1 and 20:1. In particular in the two cell lines with the lowest unspecific killing (Mino and Jeko) the highest specific contribution of the antibody to the cell killing activity was observed, in both cell lines the MOR00208 activity was statistically significant different from IgG1 control (FIG. 1). In the three cell lines with higher unspecific killing the activity profile was similar (MOR00208>IgG1 control) but specific effects were limited (FIG. 2).

Cytotoxicity Assays with Primary Patient Cells

Figure 3:
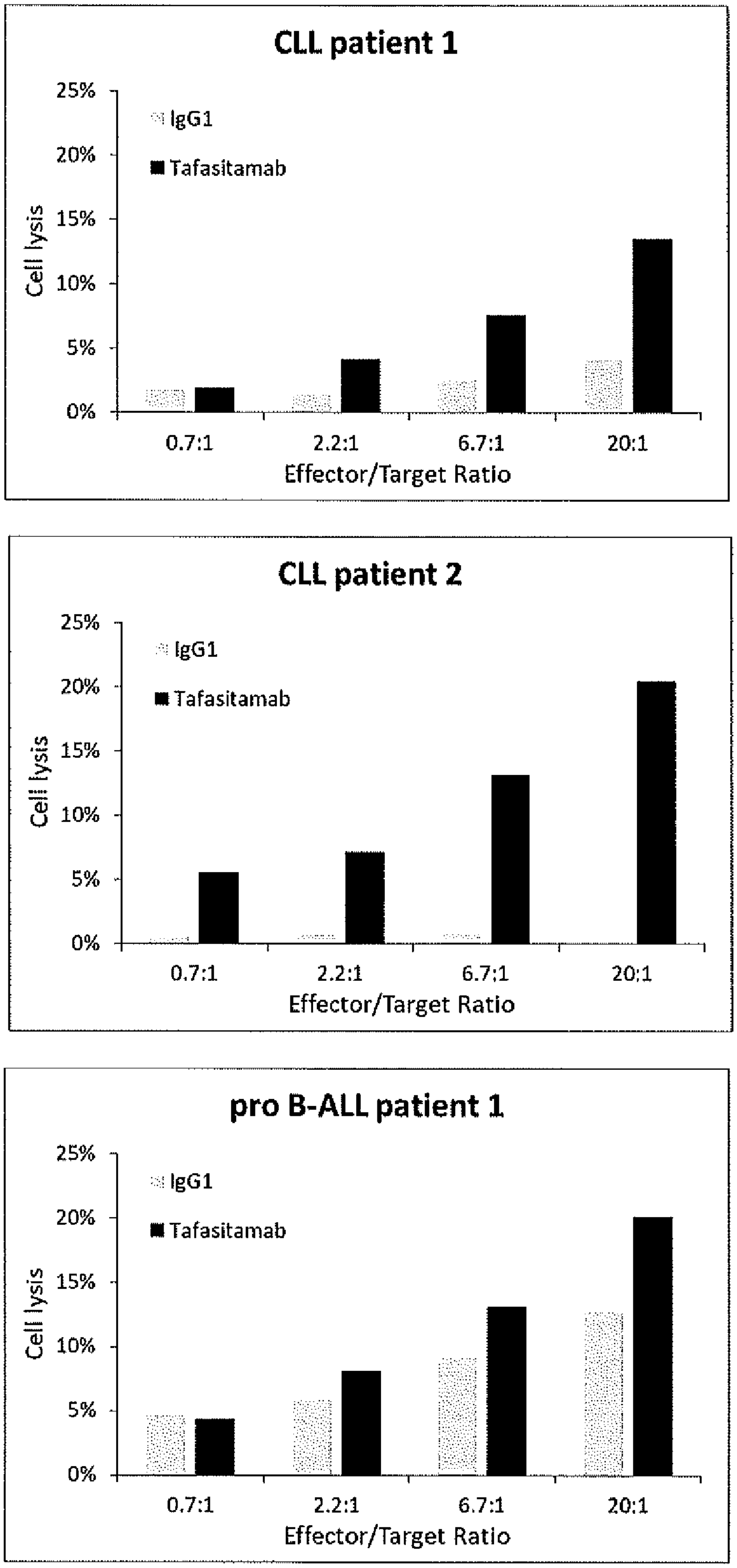
FIG. 3: Representative ADCC assays of MOR00208 at increasing effector to target cell (E:T) ratios using primary tumor cells from two CLL and one B-ALL patient as target cells. Results for specific cell killing expressed as % dead target ceils mediated by MOR00208 (black) or the IgG1 control (white) and γδ T-cells from healthy donors are depicted for three experiments using primary tumor cells as target cells. Four different E:T ratios between 0.7:1 and 20:1 were tested.
Figure 4:
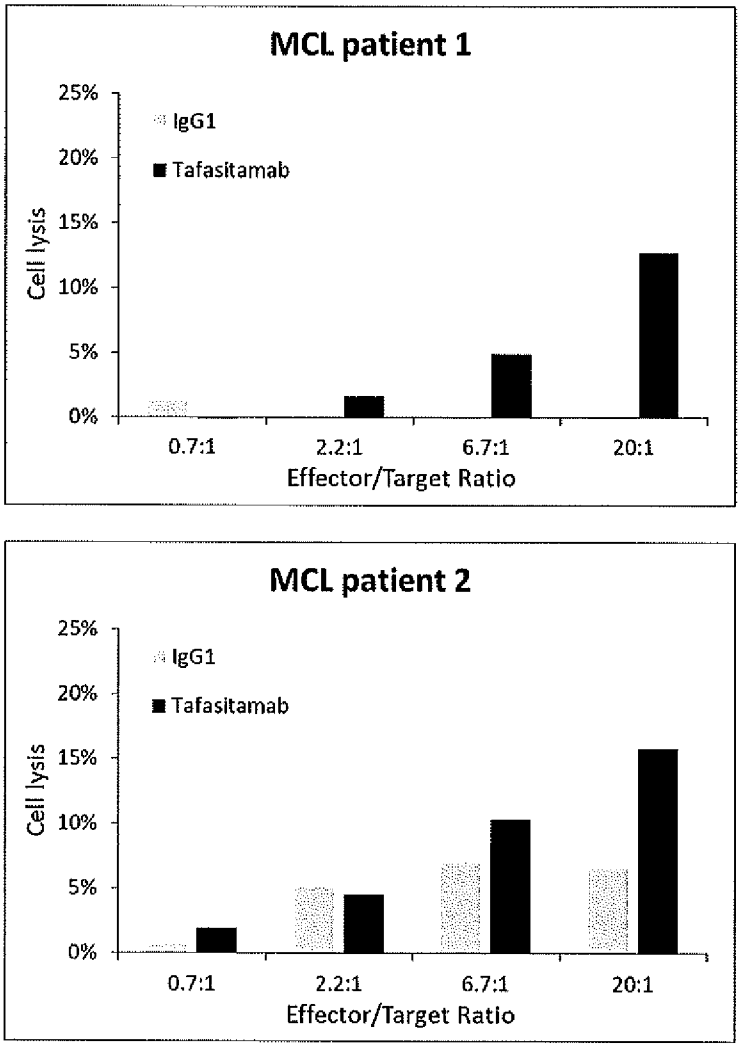
FIG. 4: Representative ADCC assays of MOR00208 at increasing effector to target cell (E:T) ratios using primary tumor cells from two MCL patients as target cells. Results for specific cell killing expressed as % dead target cells mediated by MOR00208 (black) or the IgG1 control (white) and γδ T-cells from healthy donors are depicted for three experiments using primary tumor cells as target cells. Four different E:T ratios between 0.7:1 and 20:1 were tested.

As performed with the cell Sines primary tumor cells from two CLL, two MCL and one B-ALL patient were isolated and incubated with varying E:T ratios of γδ T-cells (0.7:1 to 20:1) of a single donor as well as CD19-targeting antibodies at 1 μg/ml (FIG. 3 and FIG. 4). In line with the observation on cell lines MOR00208 showed a distinct specific contribution to killing activity of the γδ T-cells. This contribution increased with E:T ratios on all primary ceils and was most pronounced at the highest tested E:T ratio of 20:1. Primary patient cells were tested in a single experiment only.

CONCLUSION

In summary. γδ T-cells turned out to be a potential effector cell population in antibody based tumor therapy as demonstrated for the Fc-enhanced CD19-targeting antibody MOR00208 in this study. MOR00208 showed strong anti-tumor activity mediated by the presence of γδ T-cells towards several lymphoma and leukemia cell lines as well as primary patient-derived CLL, MCL and B-ALL cells and provides a sound rational for combining MOR00208 and γδ T-cells as a promising approach for lymphoma and leukemia therapy.

We claim:

1. A method for treatment of a hematological cancer in a human subject in need thereof, said method comprising administering to the subject an anti-CD19 antibody in combination with γδ T-cells, wherein the anti-CD19 antibody consists of two heavy chains and two light chains, wherein each heavy chain comprises a heavy chain variable region comprising an HCDR1 region comprising the sequence SYVMH (SEQ ID NO: 1), an HCDR2 region comprising the sequence NPYNDG (SEQ ID NO: 2), and an HCDR3 region comprising the sequence GTYYYGTRVFDY (SEQ ID NO: 3) and each light chain comprises a light chain variable region comprising an LCDR1 region comprising the sequence RSSKSLQNVNGNTYLY (SEQ ID NO: 4), an LCDR2 region comprising the sequence RMSNLNS (SEQ ID NO: 5), and an LCDR3 region comprising the sequence MQHLEYPIT (SEQ ID NO: 6), and wherein the hematological cancer is a non-Hodgkin's lymphoma or chronic lymphocytic leukemia.

2. The method of claim 1 wherein said γδ T-cells comprise an enriched γδ T-cell population.

3. The method of claim 1 wherein said γδ T-cells comprise non-engineered γδ T-cells.

4. The method of claim 1 wherein said γδ T-cells comprise engineered γδ T-cells.

5. The method of claim 1 wherein said γδ T-cells are isolated from peripheral blood.

6. The method of claim 1 wherein said γδ T-cells are isolated from tumor tissue.

7. The method of claim 1 wherein said γδ T-cells are isolated from non-hematopoietic tissue.

8. The method of claim 1 wherein said γδ T-cells are isolated from peripheral blood and were cultivated in the presence of IL-2 and ZOL.

9. The method of claim 1 wherein said γδ T-cells are blood-derived Vγ9Vδ2 T-cells.

10. The method of claim 1 wherein the anti-CD19 antibody and the γδ T cells are administered in a simultaneous manner.

11. The method of claim 1 wherein the anti-CD19 antibody and the γδ T cells are administered in a separate manner.

12. The method of claim 1 wherein the hematological cancer is a non-Hodgkin's lymphoma.

13. The method of claim 12 wherein the non-Hodgkin's lymphoma is selected from the group consisting of follicular lymphoma, small lymphocytic lymphoma, mucosa-associated lymphoid tissue, marginal zone lymphoma, diffuse large B cell lymphoma, Burkitt's lymphoma, and mantle cell lymphoma.

14. The method of claim 1 wherein the hematological cancer is chronic lymphocytic leukemia.

15. The method of claim 1 wherein the amino acid sequence of each of the heavy chain variable regions is set forth in SEQ ID NO:7 and the amino acid sequence of each of the light chain variable regions is set forth in SEQ ID NO:8.

16. The method of claim 1 wherein the amino acid sequence of each of the heavy chains is set forth in SEQ ID NO: 11 and the amino acid sequence of each of the light chains is set forth in SEQ ID NO: 12.

* * * * *